(12) United States Patent
Figley et al.

(10) Patent No.: US 11,123,739 B2
(45) Date of Patent: Sep. 21, 2021

(54) THERMAL CYCLING METHODS AND APPARATUSES FOR CARRYING OUT EFFICIENT POLYMERASE CHAIN REACTION (PCR) PROCESSES TO AMPLIFY DEOXYRIBONUCLEIC ACID (DNA)

(71) Applicant: CBF Systems Inc., Edmonton (CA)

(72) Inventors: Curtis Barry Figley, Edmonton (CA); Darin Wayne Hunt, Edmonton (CA)

(73) Assignee: CBF SYSTEMS INC., Edmonton (CA)

( * ) Notice: Subject to any disclaimer, the term of this patent is extended or adjusted under 35 U.S.C. 154(b) by 828 days.

(21) Appl. No.: 15/624,667

(22) Filed: Jun. 15, 2017

(65) Prior Publication Data

US 2018/0154363 A1 Jun. 7, 2018

Related U.S. Application Data

(60) Provisional application No. 62/488,567, filed on Apr. 21, 2017, provisional application No. 62/323,128, filed on Apr. 15, 2016.

(51) Int. Cl.
| | |
|---|---|
| *C12Q 1/68* | (2018.01) |
| *B01L 7/00* | (2006.01) |
| *C12M 1/36* | (2006.01) |
| *C12M 1/38* | (2006.01) |
| *C12N 15/09* | (2006.01) |
| *C12Q 1/686* | (2018.01) |
| *B01J 19/00* | (2006.01) |
| *B01L 9/00* | (2006.01) |
| *B01L 3/00* | (2006.01) |
| *B01L 9/06* | (2006.01) |

(52) U.S. Cl.
CPC .............. *B01L 7/52* (2013.01); *B01L 7/5255* (2013.01); *C12M 1/36* (2013.01); *C12M 1/38* (2013.01); *C12N 15/09* (2013.01); *C12Q 1/686* (2013.01); *B01J 19/00* (2013.01); *B01L 3/50851* (2013.01); *B01L 7/00* (2013.01); *B01L 9/065* (2013.01); *B01L 9/523* (2013.01); *B01L 9/527* (2013.01); *B01L 2300/0825* (2013.01); *B01L 2300/0838* (2013.01)

(58) Field of Classification Search
None
See application file for complete search history.

(56) References Cited

U.S. PATENT DOCUMENTS 6,558,947 B1 * 5/2003 Lund .................. B01L 3/50851
219/428

FOREIGN PATENT DOCUMENTS

WO WO-2006138586 A2 * 12/2006 ............. B01L 7/525

OTHER PUBLICATIONS

Wikipedia, Thermal Cycler, URL=https://en.wikipedia.org/w/index.php?title=Thermal_cycler&oldid=784159792, available at least as early as Jun. 6, 2017, 2 pages.
Wikipedia, Polymerase Chain Reaction, URL=https://en.wikipedia.org/wiki/Polymerase_chain_reaction, available at least as early as May 6, 2015, 12 pages.
W. Rychlik et al., Optimization of the annealing temperature for DNA amplification in vitro, Nucleic Acids Research, Nov. 21, 1990, 6409-6412, 18-21, doi: 10.1093/nar/18.21.6409.
D.J. Sharkey et al., Antibodies as Thermolabile Switches: High Temperature Triggering for the Polymerase Chain Reaction, Nature Biotechnology, May 1, 1994, 506-509, 12-5, doi:10.1038/nbt0594-506.
A. Chien et al., Deoxyribonucleic acid polymerase from the extreme thermophile Thermus aquaticus, Journal of Bacteriology, Sep. 1976, 1550-1557, 127-3.
F.C. Lawyer et al., High-level Expression, Purification, and Enzymatic Characterization of Full-length Thermus aquatIcus DNA Polymerase and a Truncated Form Deficient in 5' to 3' Exonuclease Activity, Genome Research, 1993, 275-287, 2-4, doi:10.1101/gr.2.4.275.
Neil A. Campbell, Biology, 7th ed., Dec. 13, 2004, pp. 391-392, Pearson Education, San Francisco.

* cited by examiner

*Primary Examiner* — Stephanie K Mummert
(74) *Attorney, Agent, or Firm* — Robert A. Nissen

(57) ABSTRACT

A thermal cycling method and associated device is described. The method is for carrying out a polymerase chain reaction (PCR) process to amplify deoxyribonucleic acid (DNA), and the method includes: pre-heating a series of blocks to respective temperatures that correspond to different respective heating stages in a PCR process, in which each block of the series of blocks defines a respective heat transfer surface, in which the series of blocks define a sequence of positions along a path, with each position defined by a respective heat transfer surface of a respective block; and moving a PCR reaction vessel, which contains deoxyribonucleic acid (DNA) and PCR reagents, along the path into and out of each respective position in the sequence of positions according to a schedule, in which, at each respective position the PCR reaction vessel is in thermal contact with the respective heat transfer surface to equilibrate a temperature of the PCR reaction vessel to a target temperature that corresponds to a respective heating stage in the PCR process.

14 Claims, 21 Drawing Sheets

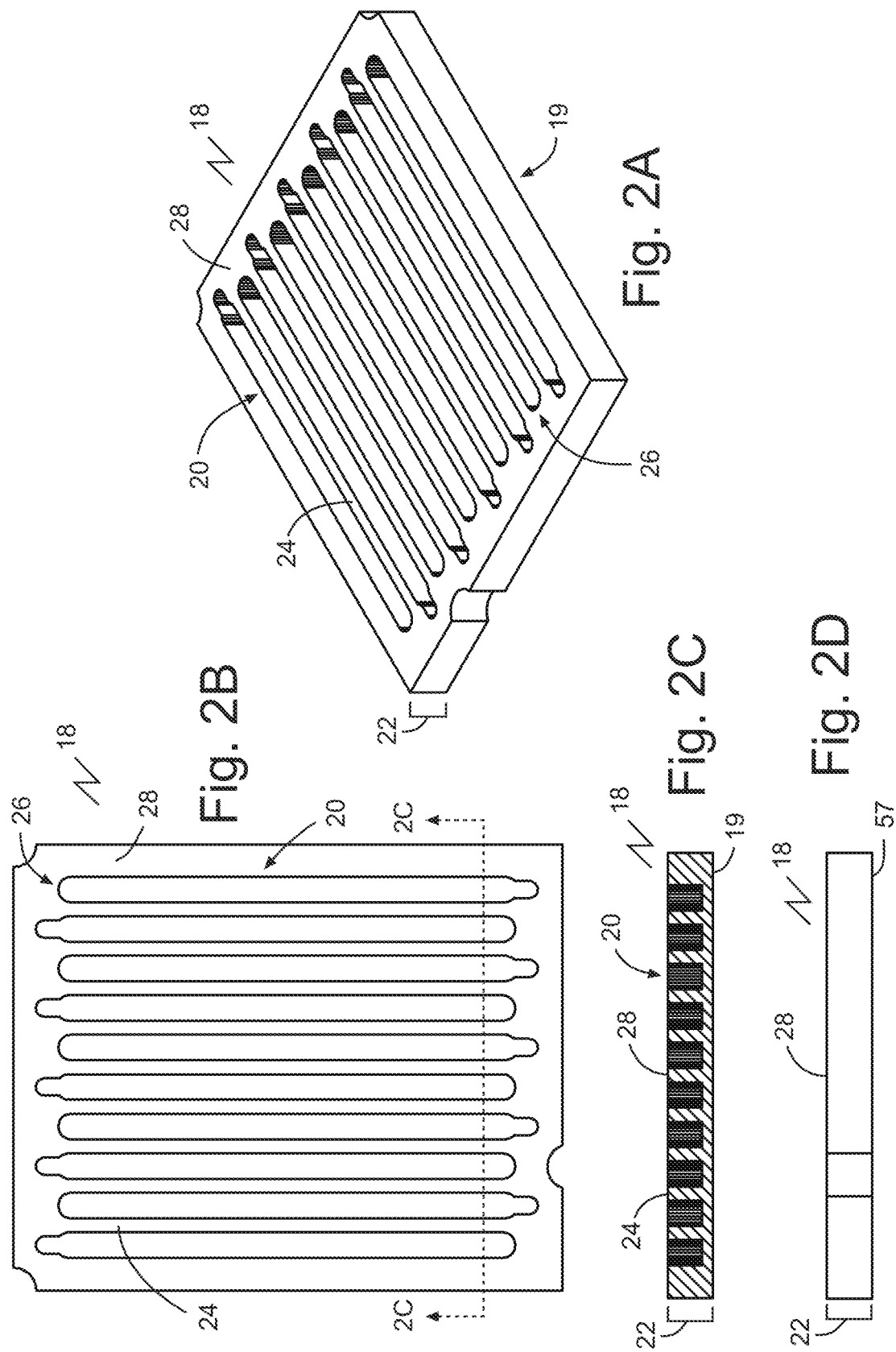

THERMAL CYCLING METHODS AND APPARATUSES FOR CARRYING OUT EFFICIENT POLYMERASE CHAIN REACTION (PCR) PROCESSES TO AMPLIFY DEOXYRIBONUCLEIC ACID (DNA)

CROSS-REFERENCE TO RELATED APPLICATIONS

This application claims the benefit under 35 USC 119(e) of U.S. provisional application Ser. No. 62/323,128 filed Apr. 15, 2016 and under 35 USC 119(e) of U.S. provisional application Ser. No. 62/488,567 filed Apr. 21, 2017.

TECHNICAL FIELD

Disclosed are thermal cycling methods and apparatuses for carrying out efficient polymerase chain reaction (PCR) processes to amplify deoxyribonucleic acid (DNA).

BACKGROUND

Modern PCR machines typically include a Peltier element that heats and cools a heating block to effect temperature changes in the PCR reaction medium. Quality thermal cyclers often contain metal heating blocks to achieve uniform temperature throughout the heating zone. Other cyclers have multiple heating zones with high heat capacity, each of which is kept at a constant temperature, and liquid flow PCR reaction media are circulated through channels in each heating zone by means of an automated process. Miniaturized thermal cyclers have been created in which the reaction mixture moves via channels through hot and cold zones on a microfluidic chip.

SUMMARY

In some cases devices and methods are disclosed for rapid thermal cycling of PCR samples.

A thermal cycler is disclosed for carrying out a polymerase chain reaction (PCR) process to amplify deoxyribonucleic acid (DNA), the thermal cycler comprising: a series of blocks that each define a respective heat transfer surface, in which the series of thermal storage blocks define a sequence of positions along a path, with each position defined by a respective heat transfer surface of a respective block, in which each block is associated with a respective heating system; a PCR reaction vessel; an actuator connected to the PCR reaction vessel; and a controller connected to send control signals to: a) the respective heating systems to pre-heat the series of blocks to respective temperatures that correspond to different respective heating stages in a PCR process; and b) the actuator to cause the actuator to move the PCR reaction vessel along the path into and out of each respective position in the sequence of positions according to a schedule, in which, at each respective position the PCR reaction vessel is in thermal contact with the respective heat transfer surface to equilibrate a temperature of the PCR reaction vessel to a target temperature that corresponds to a respective heating stage in the PCR process.

A thermal cycling method is disclosed for carrying out a polymerase chain reaction (PCR) process to amplify deoxyribonucleic acid (DNA), the method comprising: pre-heating a series of blocks to respective temperatures that correspond to different respective heating stages in a PCR process, in which each block of the series of blocks defines a respective heat transfer surface, in which the series of blocks define a sequence of positions along a path, with each position defined by a respective heat transfer surface of a respective block; and moving a PCR reaction vessel, which contains deoxyribonucleic acid (DNA) and PCR reagents, along the path into and out of each respective position in the sequence of positions according to a schedule, in which, at each respective position the PCR reaction vessel is in thermal contact with the respective heat transfer surface to equilibrate a temperature of the PCR reaction vessel to a target temperature that corresponds to a respective heating stage in the PCR process.

A thermal cycling method is disclosed for accomplishing PCR DNA amplification using a series of high thermal capacity, high thermal conductivity hot blocks that act as thermal energy sinks to effect rapid heating and cooling of a vessel containing PCR reagents and DNA samples where said method includes the steps of: a) preheating the series of hot blocks to temperatures close to the target temperatures of the intended PCR sequence; b) placing a PCR vessel loaded with reagents and DNA samples onto such hot blocks; c) manipulating said PCR vessel between the hot blocks in a defined sequence to allow the hot blocks to heat or cool the PCR vessel and its contents according to a schedule; d) coordinating the movement of the PCR vessel with a schedule for the individual hot block temperature set points, such that the hot blocks are variously pre-biased, preheated or pre-cooled according to said temperature schedule by an amount that allows the PCR vessel and hot block, once mated for the intended PCR stage, to equalize near the intended target temperature for the associated PCR step, and e) determining the amount of temperature pre-bias to apply to each hot block based upon the relative thermal masses of the PCR vessel and hot block.

A thermal cycling device is disclosed for accomplishing PCR DNA amplification where said device uses a series of high thermal capacity, high thermal conductivity hot blocks acting as thermal energy sinks to effect rapid heating and cooling of a vessel containing PCR reagents and DNA samples, where said device includes features to: a) preheat a series of hot blocks to temperatures close to the programmed target temperatures for the PCR sequence; b) hold the PCR vessel loaded with reagents and DNA samples against such hot blocks; c) move said PCR vessel between the hot blocks in a controlled sequence so the hot blocks heat or cool the PCR vessel and its contents between different programmed target temperatures; and d) coordinate the movement of the PCR vessel with the setting of the hot block temperatures such that the hot blocks are variously pre-biased, preheated or pre-cooled according to the programmed schedule so that once mated, the PCR vessel and hot block equalize to the programmed target temperature for the associated PCR step.

In various embodiments, there may be included any one or more of the following features: Each heat transfer surface is defined by an external face of the respective block. In each respective position, a base heat transfer surface of the PCR reaction vessel is in thermal contact with the respective heat transfer surface, which faces up. The PCR reaction vessel sits on and above the respective heat transfer surface of the block. Moving further comprises sliding the PCR reaction vessel laterally between blocks. The heat transfer surfaces define a common plane in which the path is defined. Each block in the series of blocks is thermally isolated from adjacent blocks. Moving is carried out by an actuator, which is connected to a controller that implements the schedule. The actuator comprises a linear screw actuator. Moving comprises moving the PCR reaction vessel between one or more of: a first position where the PCR reaction vessel is in thermal contact with a first block that equilibrates the PCR reaction vessel at a first target temperature sufficient to denature the DNA; a second position where the PCR reaction vessel is in thermal contact with a second block that equilibrates the PCR reaction vessel at a second target temperature sufficient to anneal primers to denatured DNA; and a third position where the PCR reaction vessel is in thermal contact with a third block that equilibrates the PCR reaction vessel at a third target temperature sufficient to cause polymerized extension of the DNA. Pre-heating comprises, prior to the PCR reaction vessel moving into thermal contact with a respective heat transfer surface, pre-biasing the respective temperature of the respective block either above or below a respective target temperature that corresponds to the respective heating stage in the PCR process. Pre-biasing comprises pre-biasing the respective temperature of a respective hot block either: below the respective target temperature if the PCR reaction vessel has a temperature that is higher than the respective target temperature as the PCR reaction vessel moves into the respective position; or above the respective target temperature if the PCR reaction vessel has a temperature that is lower than the respective target temperature as the PCR reaction vessel moves into the respective position. The magnitude of bias above or below the target temperature is sufficient to store or remove sufficient heat, such that once the block and vessel are mated, the two masses of the hot block and PCR reaction vessel converge on the target temperature for that PCR stage without addition of heat to, or removal of heat from, the block. Upon making thermal contact with the PCR reaction vessel, the respective block that was previously pre-biased above or below the temperature of the respective block is subsequently maintained at the respective target temperature. The magnitude of pre-bias is selected to prevent the PCR reaction vessel from: overshooting the respective target temperature in the case where the respective block is pre-biased above the respective target temperature; and undershooting the respective target temperature in the case where the respective block is pre-biased below the respective target temperature. The magnitude of pre-bias is selected to minimize the amount of time it takes the PCR reaction vessel to reach the respective target temperature after thermal contact with the respective block, in which the pre-bias is calculated based on the temperature of the incoming PCR reaction vessel, and the relative thermal masses of the PCR reaction vessel and the respective block. A transitional block is positioned adjacent and upstream of a respective position along the path, and further comprising, before the PCR reaction vessel reaches the respective position, pre-heating or pre-cooling the PCR reaction vessel in the direction of a respective target temperature at the respective position by heat transfer across a heat transfer surface of the transitional block as the PCR reaction vessel comes into thermal contact with the transitional block, wherein the transitional block provides an intermediate source or sink of thermal energy to accelerate temperature slewing. The respective block at the respective position is pre-heated to the respective target temperature. Each block of the series of blocks is maintained in a pre-heated state when not in contact with the PCR reaction vessel. A thermal mass of each block is between 1:1 and 100:1 relative to a thermal mass of the PCR reaction vessel. The thermal mass of each block is between 15:1 and 35:1 relative to a thermal mass of the PCR reaction vessel. Each block is made of thermally conductive metal. Each block is made of relatively high thermal conductivity and high thermal capacity metal. The PCR reaction vessel is made of relatively high thermal conductivity metal. Each block and the PCR reaction vessel are made of the same material. Each block and the PCR reaction vessel may be made of different high thermal conductivity materials or combinations of high thermal conductivity materials. One or both of corresponding heat transfer surfaces of the block and the PCR reaction vessel are shaped to increase surface area relative to a planar surface. One or both the corresponding heat transfer surfaces of the block and the PCR reaction vessel comprise heat transfer fins or grooves. Corresponding heat transfer surfaces of the block and the PCR reaction vessel are structured with complementary nesting shapes. Corresponding heat transfer surfaces of the block and the PCR reaction vessel are planar in shape. The PCR reaction vessel forms a plate that defines an external heat transfer surface. The series of blocks are arranged in a loop, an arc, or a linear array, and an actuator directs the movement of the PCR reaction vessel along the shape of path defined by the blocks. Carrying out plural cycles of the moving stage. The series of blocks, actuator, and PCR reaction vessel are oriented such that during operation the actuator slides the PCR reaction vessel laterally between blocks, such that in each respective position a base heat transfer surface of the PCR reaction vessel rests in thermal contact on and above the respective heat transfer surface, which faces up. The controller is configured to send control signals to the respective heating systems to, prior to the PCR reaction vessel moving into thermal contact with a respective heat transfer surface, pre-bias the respective temperature of the respective block either: below the respective target temperature if the PCR reaction vessel in use has a temperature that is higher than the respective target temperature as the PCR reaction vessel moves into the respective position; or above the respective target temperature if the PCR reaction vessel in use has a temperature that is lower than the respective target temperature as the PCR reaction vessel moves into the respective position. The PCR reaction vessel comprises desiccated PCR reagents. Each block comprises a respective temperature sensor. The relative thermal masses of the hot block to PCR vessel are in the ratio range of 1:1 to 100:1. The PCR vessel is configured to mate readily to the hot block to provide intimate thermal contact to rapidly and efficiently conduct heat between the hot block and the PCR vessel contents and where such configuration includes one or more of: a) having a broad aspect for mating to the surface of a heating or cooling stage and is thin in the direction normal to this surface (in this geometry the PCR reaction vessel is herein referred to as a "PCR cassette" or simply a "cassette"); b) is constructed of high thermal conductivity materials; c) provides locations to process multiple PCR tests within the same PCR vessel; d) contains heat conduction enhancement features to increase the contact area and coupling effectiveness between the broad aspect mating surface and the PCR reagents and DNA samples; and e) results in a small but predictable and consistent thermal mass so that temperature pre-bias settings are consistent between loaded PCR vessels. The PCR vessel moves along a linear arrangement of hot blocks. The PCR vessel moves around a circular arrangement of hot blocks to reduce the effects introduced by the direction of travel changes induced moving on and off the hot blocks at the ends of linear arrangement. The PCR vessel includes desiccated PCR reagents so that the PCR vessel can be filled with re hydrating DNA containing solution. The time evolution of the temperature detected at the hot block immediately following the arrival of a PCR vessel onto the block is used as a diagnostic to assess the quality of thermal contact made with the PCR vessel and where such diagnostic information is used to extend the dwell time if poorer contact is detected. Hot blocks are configured in functional pairs targeting heating the PCR reaction vessel to the same ultimate settling temperature (target temperature) and where one element of a pair is used as a final temperature stabilization point and the other is used in a pre-bias mode to effect accelerated temperature changes. The PCR vessel is configured to mate intimately to the hot block and to provide a high degree of thermal coupling to the PCR volume to effect rapid and accurate temperature manipulation of the PCR vessel contents and where such configuration includes one or more of: a) a broad mating surface aspect between the hot block and PCR vessel to enhance thermal contact; b) hot blocks and PCR vessels fabricated from high thermal conductivity materials; c) a PCR vessel configured to hold multiple PCR tests; d) a PCR vessel that has thermal fin features to increase the contact area between the PCR process materials and the high thermal conductivity PCR vessel material; and e) well defined thermal masses so that temperature pre-bias settings can be consistently established. The PCR vessel moves along a linear arrangement of hot blocks. The PCR vessel moves around a circular arrangement of hot blocks to mitigate on and off transition effects caused by direction reversals on hot blocks. The PCR vessel includes desiccated PCR reagents so that the PCR vessel can be filled with rehydrating DNA containing solution.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which:

FIG. 2A is a perspective view of a polymerase chain reaction (PCR) cassette. The cassette 18 may comprise a highly thermally conductive material. Cassette 18 may have channels 26 to hold the sample material.

FIG. 2B is a top plan view of the PCR cassette of FIG. 2A.

FIG. 2C is a section view taken along the 2C-2C section lines from FIG. 2B.

FIG. 2D is a front end view of the PCR cassette of FIG. 2A.

FIG. 6 shows how the temperature of the heater block may change quickly when a cassette having a lower temperature moves onto the block. The shape of the temperature transition depends on a number of factors including the quality of the thermal bond between the cassette and the block. The temperature as a function of time is shown for the cases of a good thermal contact and a poor thermal contact.

FIG. 9D is a perspective view of the PCR cassette of FIG. 9A.

FIG. 9E is a bottom view of the PCR cassette of FIG. 9A.

FIG. 9F is a perspective view of the PCR cassette of FIG. 9A.

FIG. 9G is a side elevation view of the PCR cassette of FIG. 9A.

FIG. 10 is a drawing of an operational prototype PCR system physical arrangement having heater blocks 10, cassette position control, a viewing mirror 51, and an epifluorescence assembly or camera system. Power supplies and control electronics may be housed inside the enclosure.

FIG. 11 shows the temperature in the PCR sample in the cassette as measured by a small thermistor mounted within the central region of the PCR reaction volume in a cassette channel during repeated thermal cycling.

FIG. 12 shows the temperature in the PCR sample in the cassette as measured by a small thermistor within the central region of the PCR reaction volume in a cassette channel during thermal cycling.

FIG. 13 shows the temperature in the PCR sample in the cassette as measured by a small thermistor during the extension step of a PCR thermal cycle.

DETAILED DESCRIPTION

Immaterial modifications may be made to the embodiments described here without departing from what is covered by the claims.

In the art of molecular biology, polymerase chain reaction (PCR) is a well-known process used to amplify low concentration genetic material so that various chemical and biochemical tests can be performed. The most general form of the PCR as described in various written texts and online resources uses repeated cycles of heating and cooling, commonly known as "thermal cycling", to repeatedly duplicate deoxyribonucleic acid (DNA) using replication enzymes. The target DNA is mixed in with a surplus of short fragments of DNA called "primers" containing complimentary chemical sequences to the target region of DNA and DNA polymerase so that selective amplification is accomplished during each thermal cycle. As the thermal cycling progresses, DNA replicated in previous steps is also replicated. Notionally, as long as the replication reagents are in surplus, the targeted DNA concentrations grow stepwise exponentially with each cycle.

Figure 17:
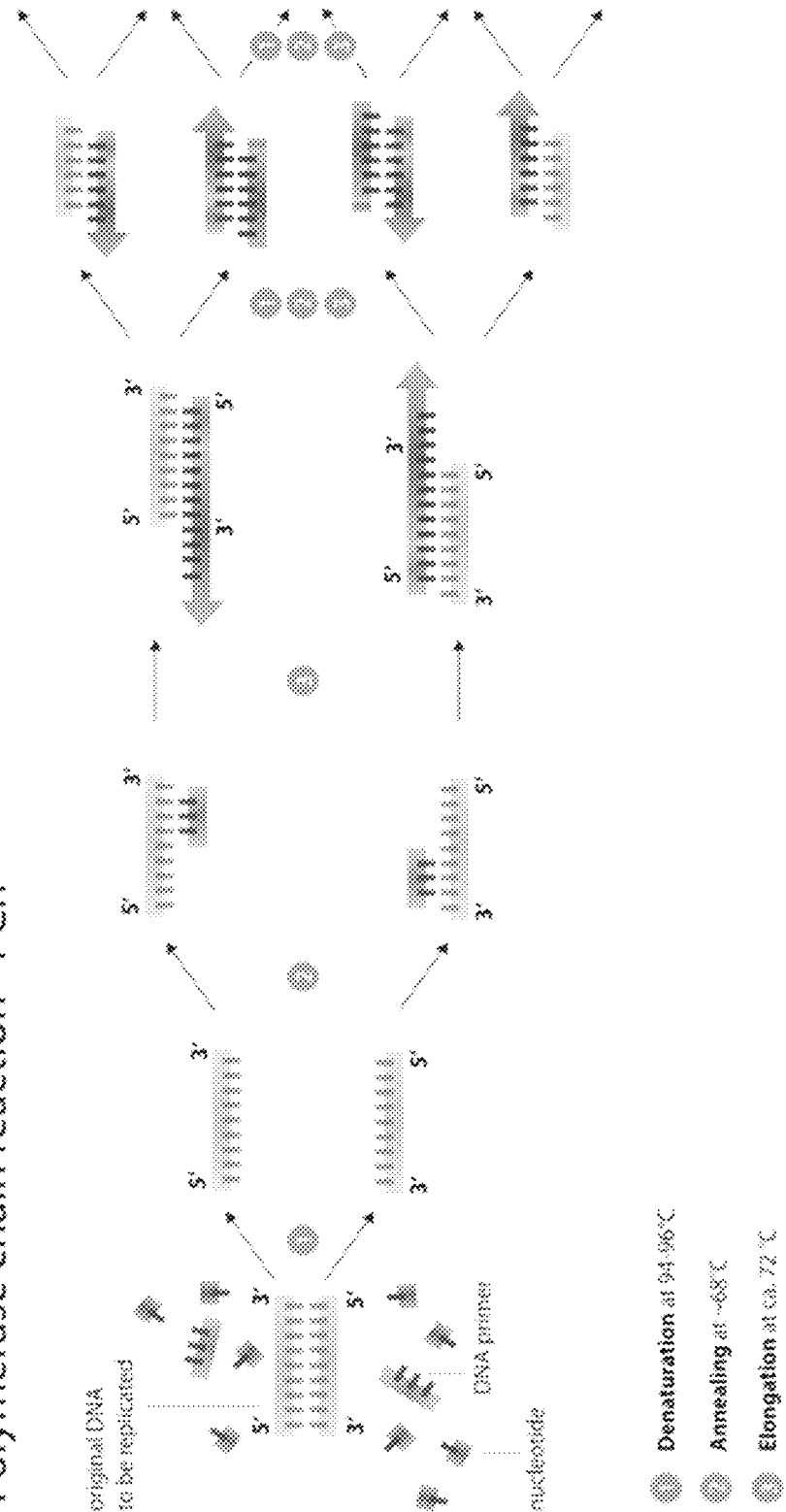
FIG. 17 is a flow diagram of a polymerase chain reaction.

Referring to FIG. 17, typically, PCR consists of a series of 20-40 repeated temperature changes, called cycles, with each cycle commonly consisting of 2-3 discrete temperature steps, usually three. The cycling is often preceded by a single temperature step at a high temperature (>90° C.), and followed by one hold at the end for final product extension or brief storage. The temperatures used and the length of time they are applied in each cycle depend on a variety of parameters. These include the enzyme used for DNA synthesis, the concentration of divalent ions and deoxynucleotides (dNTP) in the reaction, and the melting temperature (Tm) of the primers.

A PCR process may have an initialization step (only required for DNA polymerases that require heat activation by hot-start PCR.). This step consists of heating the reaction to a temperature of 94-96° C. (or 98° C. if extremely thermostable polymerases are used), which is held for 1-9 minutes.

A PCR process may have a denaturation step. This step is the first regular cycling event and consists of heating the reaction to 94-98° C. for 20-30 seconds. It causes DNA melting of the DNA template by disrupting the hydrogen bonds between complementary bases, yielding single-stranded DNA molecules.

A PCR process may have an annealing step: The reaction temperature is lowered to 50-65° C. for 20-40 seconds allowing annealing of the primers to the single-stranded DNA template. This temperature must be low enough to allow for hybridization of the primer to the strand, but high enough for the hybridization to be specific, i.e., the primer should only bind to a perfectly complementary part of the template. If the temperature is too low, the primer could bind imperfectly. If it is too high, the primer might not bind.

Typically the annealing temperature is about 3-5° C. below the Tm of the primers used. Stable DNA-DNA hydrogen bonds are only formed when the primer sequence very closely matches the template sequence. The polymerase binds to the primer-template hybrid and begins DNA formation. It is very vital to determine the annealing temperature in PCR. This is because in PCR, efficiency and specificity are affected by the annealing temperature. An incorrect, annealing temperature will cause an error in the test, hence high accuracy, stability and minimal over or undershoot during annealing may be important to obtaining good PCR performance.

A PCR process may have an extension/elongation step. The temperature at this step depends on the DNA polymerase used. Taq polymerase has its optimum activity temperature at 75-80° C., and commonly a temperature of 72° C. is used with this enzyme. At this step the DNA polymerase synthesizes a new DNA strand complementary to the DNA template strand by adding dNTPs that are complementary to the template in 5' to 3' direction, condensing the 5'-phosphate group of the dNTPs with the 3'-hydroxyl group at the end of the nascent (extending) DNA strand. The extension time depends both on the DNA polymerase used and on the length of the DNA fragment to amplify. As a rule-of-thumb, at its optimum temperature, the DNA polymerase polymerizes a thousand bases per minute. Under optimum conditions, i.e., if there are no limitations due to limiting substrates or reagents, at each extension step, the amount of DNA target is doubled, leading to exponential (geometric) amplification of the specific DNA fragment.

A PCR process may have a final elongation step. This single step is occasionally performed at a temperature of 70-74° C. (this is the temperature needed for optimal activity for most polymerases used in PCR) for 5-15 minutes after the last PCR cycle to ensure that any remaining single-stranded DNA is fully extended.

A PCR process may have a final hold step. This step at 4-15° C. for an indefinite time may be employed for short-term storage of the reaction.

The PCR process may be divided into three stages: exponential amplification, leveling off, and plateau. At the exponential amplification stage, at every cycle, the amount of product is doubled (assuming 100% reaction efficiency). The reaction is very sensitive. Only minute quantities of DNA must be present. At the leveling off stage, the reaction slows as the DNA polymerase loses activity and as consumption of reagents such as dNTPs and primers causes them to become limiting. At the plateau stage, no more product accumulates due to exhaustion of reagents and enzyme.

Other undesired and competing reactions occur in parallel with the intended PCR. These reactions may impair or degrade the PCR measurement in a number of ways including potentially amplifying other sections or segments of the DNA, damaging DNA so that it does not replicate, may deplete the PCR reagents, or otherwise produce confounding effects. Many of these other reactions are strongly dependent on temperature and dwell time, so it is generally beneficial to limit the time spent slewing between and dwelling at the higher temperature steps in the PCR sequence.

Furthermore, a number of the intended PCR products are only produced in significant amounts at temperatures close to where the DNA may begin to decompose or otherwise be damaged. Because of the exponential nature of the amplification, even short excursions above the target PCR melting point temperatures, especially early on in the sequence, can significantly degrade the overall amplification factor. Further, DNA that is damaged by overheating may still participate in the replication process, but may not be tagged properly thus consuming reagents and potentially introducing spurious DNA results in later DNA quantification steps. In practice this means that there is a narrow temperature target zone where effective DNA melting can occur.

As a result of the two mechanisms just discussed, it may be important that the PCR thermal sequencing process be accurately temperature controlled in terms of under and over shoot, slew rate and dwell time at the target temperature.

Many schemes and devices to carry out the PCR thermal cycling steps have been disclosed in the molecular chemistry literature or have been produced as commercial devices. These include a variety of Peltier heater based stages, multi-well microtiter plate systems, water bath configurations, chip scale microfluidic systems and other such means to heat and cool the PCR materials vessels. Many of these techniques suffer from issues related to the previously mentioned temperature under and overshoot, or they produce relatively slow temperature slew rates, or they may require long settling times to allow the temperature at the PCR reaction point to settle, or they may not be suitable for portable systems where low power is mandated. These problems are confounded by the particular heating or cooling power production methods utilized, by the heat transfer media and by the thermal behaviour of the PCR vessel materials and mechanical geometry.

Various schemes that have been disclosed that describe physically moving PCR reagents through constant temperature stages or alternately, moving constant temperature stages to accomplish a sequential PCR amplification. These arrangements include moving microfluidic channels or vessels relative to hot plates (either or both can move), flowing or shuttling reagents through capillary tubes coupled to preheated temperature sinks so that the fluid PCR mixture is alternately exposed to different temperatures, or holding PCR mixtures trapped in flow tubes against moving hot stages. In all of these disclosed schemes, the PCR mixtures were encased in a relatively low thermal mass wells or flow channels which were then placed in contact with a constant temperature controlled thermal mass or routed against such a mass as to cause the desired temperature shifts to accomplish PCR.

In the disclosure herein, an individual PCR test or sets of PCR tests may be performed inside a PCR vessel that by design typically has (but not exclusively or limited to) a small, but specifically non-trivial thermal mass with respect to the thermal mass of the heater blocks and where the volumes where PCR reactions occur in the PCR vessel are shaped to provide highly conductive heat channels between the surface contacting the heater block and the volumes where the PCR reactions occur with the express intent of one or more of:

a. using the high thermal conductivity to rapidly homogenize the temperature and thus the heating history imposed on a given volume of PCR material within one sample volume so that uniform chemical reactions are supported throughout the extent of that sample volume (that is, consistency on a local scale);

b. causing many such adjacent PCR volumes to experience the same relative thermal history, including ensuring that any process controls included in the batch are treated identically to the true samples, affecting an array of simultaneous and thermally identical controlled tests (that is, consistency at the scale of the array);

c. specifically, not operating the thermal heater blocks in a fixed temperature mode between thermal cycle steps, that is, the temperatures are intentionally steered to various controlled set points in coordination with movement of the PCR vessel;
d. providing a mechanism to rapidly load such PCR volumes with active samples, typically using conventional manual or automated dispensing techniques known to the art;
e. providing a mechanism to provide replaceable PCR volumes, such replacements potentially being precharged with the necessary reagents to conduct the PCR so that only a prepared sample needs to be loaded;
f. providing such a reaction vessel wherein the resulting PCR reaction products can be analyzed using an optical detection melt curve process such as is known in the art; and
g. where such PCR vessels are simple, inexpensive and disposable so that cleaning and purging of the PCR vessel to prevent cross contamination from run to run is unnecessary;
and wherein the non-trivial thermal mass used as the reaction vessel is coupled to the thermally controlled heat sinks in such a way as to produce predictable and repeatable thermal transient behaviour and so that the thermal slewing times are fast.

Given a uniform, predictable and repeatable thermal response, simple compensation techniques can be employed to ensure fast and accurate temperature compliance of the PCR processing volumes, one such scheme discussed herein as pre-biasing.

It may also be desirous from many application perspectives that the PCR be done as quickly as possible so that the information thus obtained can be put to use to facilitate other decisions. In particular, this is the case in situations where life, safety and security are at stake. For instance, in a clinical application where rapidly identifying the type of infectious bacteria would impact a physician's recommendations regarding a patient's course of treatment or prescribed pharmaceuticals, or that determine the status of a potentially contagious individual, rapid determination of the contagion would result in more immediate and accurate medical responses. Similar arguments can be made for many other applications where rapid testing capabilities are desired as such food safety inspections; veterinary or agricultural testing; for customs and border security checks on travelers and shipped goods; for environmental assessment of air, water and soil contamination; and potentially even in areas such as pathology and forensic investigations where determining if a dangerous pathogen is present may impact the response of emergency and military personnel. In all these areas, rapid and accurate determination of a potential biological contamination agent is critical to an effective response.

Another problem encountered with previous PCR thermal cycling approaches that are based on a single heater-cooler stage is one of temperature profile compliance accuracy. Typically in these, as heating and cooling slew rates are increased, accuracy and stability suffer. Temperature over and undershoot is common at the actual sample location, occurring due to various thermal resistances and thermal capacitances that produce lag and latency issues, temperature gradients and inconsistent temperature histories at different reaction zones. The net effect is to vary biochemical reaction rates and recruit reaction mechanisms in inconsistent fashions. In practice, this can lead to numerous performance limiting issues including but not limited to, sample and reagent degradation if spatial and temporal temperature spikes are encountered; unnecessary sample dehydration and reagent out-gassing with the potential for spot boiling at higher target temperature points; denaturing of the DNA replication reagents; introduction of micro-bubbles in the sample regions which reduces reagent mobility and mixing within the sample volume as well as alters the thermal conductivity of the sample zone which in turn results in further temperature control issues; may open up other biochemical and chemical reaction channels that degrade the overall performance of the final DNA detection by adding noise and other confounding signals or that depress the signal strength of the intended DNA detection signal.

A useful PCR thermal cycling system may rapidly heat and cool to exact set points, with little or no over or undershoot, and in such a way as to heat and cool the entire volume of the PCR reagents in unison.

A useful PCR thermal cycling system may provide for improved amplification at each cycle since excursions above the intended Denaturation temperatures are reduced. This allows more precise control and setting of the target Denaturation temperature without introducing higher risks of DNA damage or dimer production while allowing cycle gains closer to "2" to be achieved. Thus fewer cycles are required to achieve a particular final amplification gain resulting in a higher effective signal to noise capability. This also has the effect of reducing net processing time. Improved amplification performance is an advantage of some embodiments of this disclosure.

A further issue with many applications is that ideally the device should provide the opportunity to simultaneously process many samples in parallel and with the same thermal profiles being imposed on all the samples. This capability is critical where simultaneous process verification and quality control samples are included as part of the overall sample suite, as is the case for many safety and diagnostic applications. In some cases embodiments of the disclosure provide mechanisms to process many samples simultaneously in parallel under functionally identical thermal conditions.

In some cases embodiments of the disclosure provide improved power and energy efficiency and simplified temperature control requirements.

Because embodiments of the disclosure establish the thermal elements responsible for the bulk heating and cooling of the PCR mixture at relatively consistent temperatures (but specifically, not constant temperatures), energy losses and peak power associated with techniques that rapidly pump the large mass of the thermal stage between different temperatures may be avoided. Maintenance of several different temperatures zones generally requires less absolute power than actively steering the temperature of a single zone rapidly between significantly different set points as is the case with for example with Peltier based thermal cyclers or traditional gas phase heat pumps, or by exhausting any heat required to be removed during rapid temperature swings using forced air blowers. This aspect of the disclosure is particularly important for portable and mobile applications where higher power delivery rates, higher power rejection rates and higher total energy requirements dictate larger battery stores or shorter system operating times.

The use of comparatively large and highly conductive thermal storage masses (or heat sinks) for the hot blocks reduces the natural frequency of the system and hence the frequency response demands on the temperature control schemes needed to achieve good set point compliance. Large hot block thermal capacities with high thermal conductivity act to slow temperature fluctuations so that low frequency control operation is sufficient (for example, simple ON/OFF (bang-bang) heat-cool techniques).

Figure 1A:
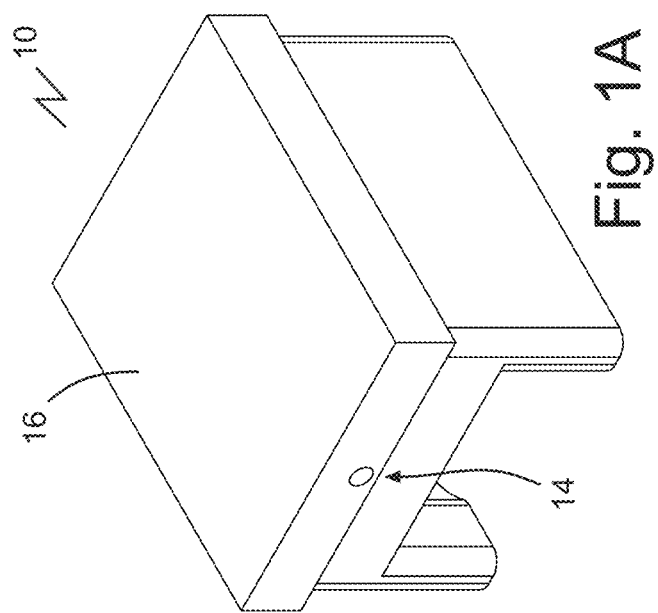
FIG. 1A is a perspective view of a single hot block element. This element may be a highly thermally conductive block 10 that may have a large thermal mass compared to the PCR reagent vessel (cassette 18) containing the sample. The temperature of the block may be controlled so that when the cassette 18 is moved on to the block 10, the cassette 18 temperature may be changed to the desired temperature. A temperature sensor 12 may be placed in a channel, for example a sensor channel 14, near the top of the block and may measure the temperature near the surface, for example surface 16 on which cassette 18 is placed.
Figure 1B:
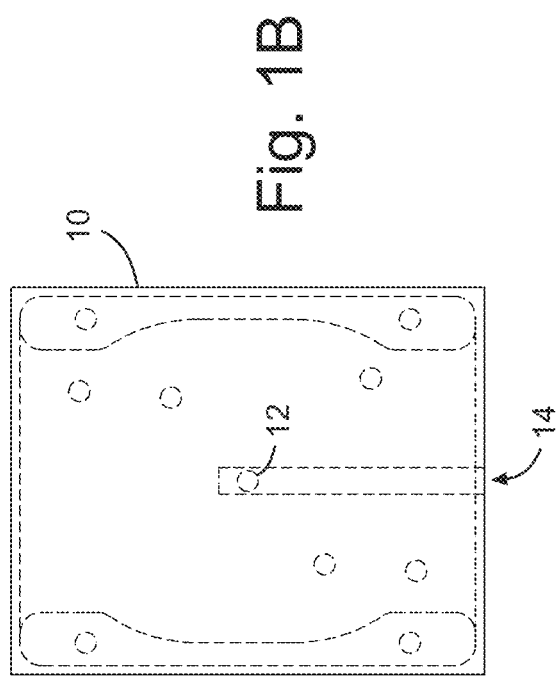
FIG. 1B is a top plan view of the hot block of FIG. 1A, with dotted lines to indicate internal structure.
Figure 1C:
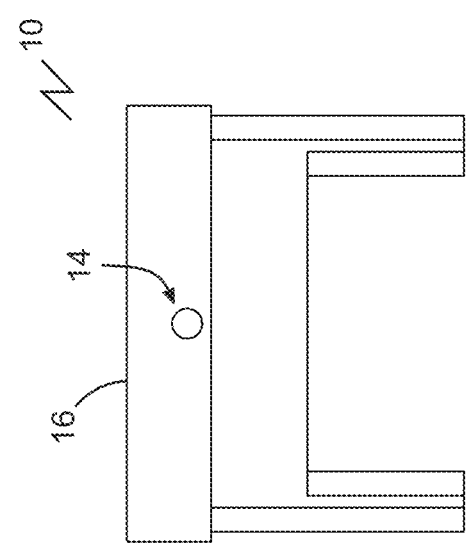
FIG. 1C is a front view of the hot block of FIG. 1A.
Figure 3B:
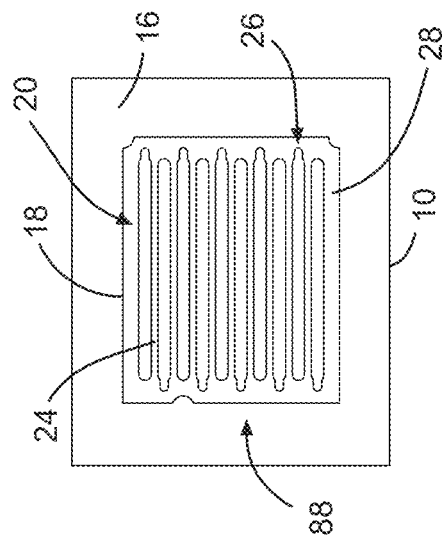
FIG. 3B is a top plan view of the PCR cassette and the hot block of FIG. 3A.
Figure 3D:
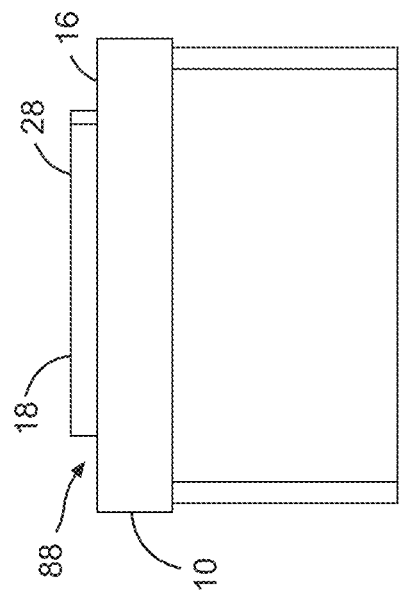
FIG. 3D is a side elevation view of the PCR cassette and the hot block of FIG. 3A.
Figure 3A:
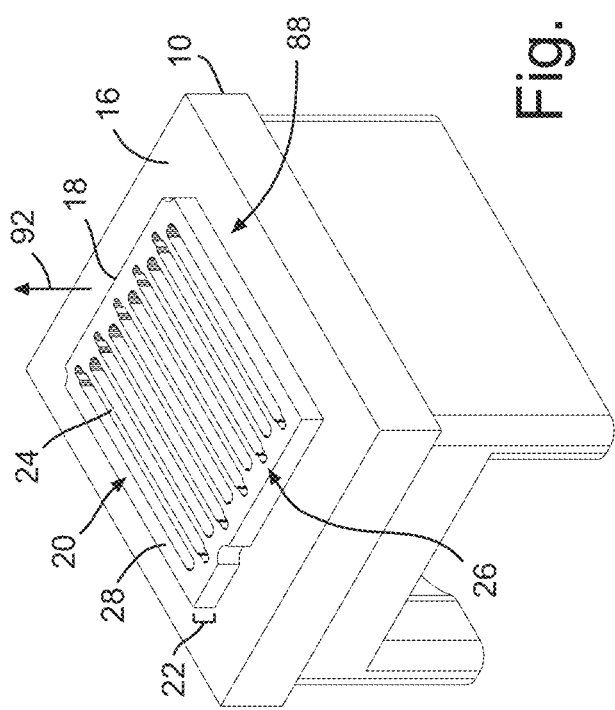
FIG. 3A is a perspective view of a PCR cassette on a hot block.
Figure 3C:
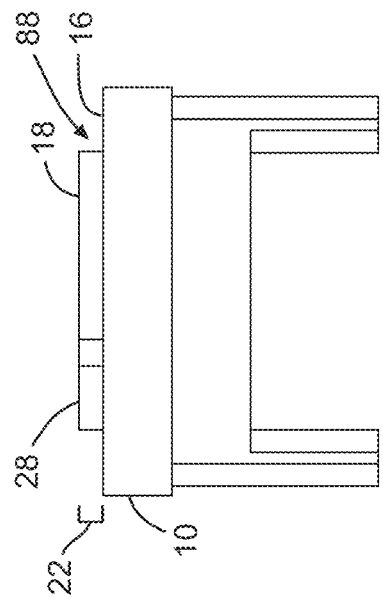
FIG. 3C is an end view of the PCR cassette and the hot block of FIG. 3A.
Figure 4:
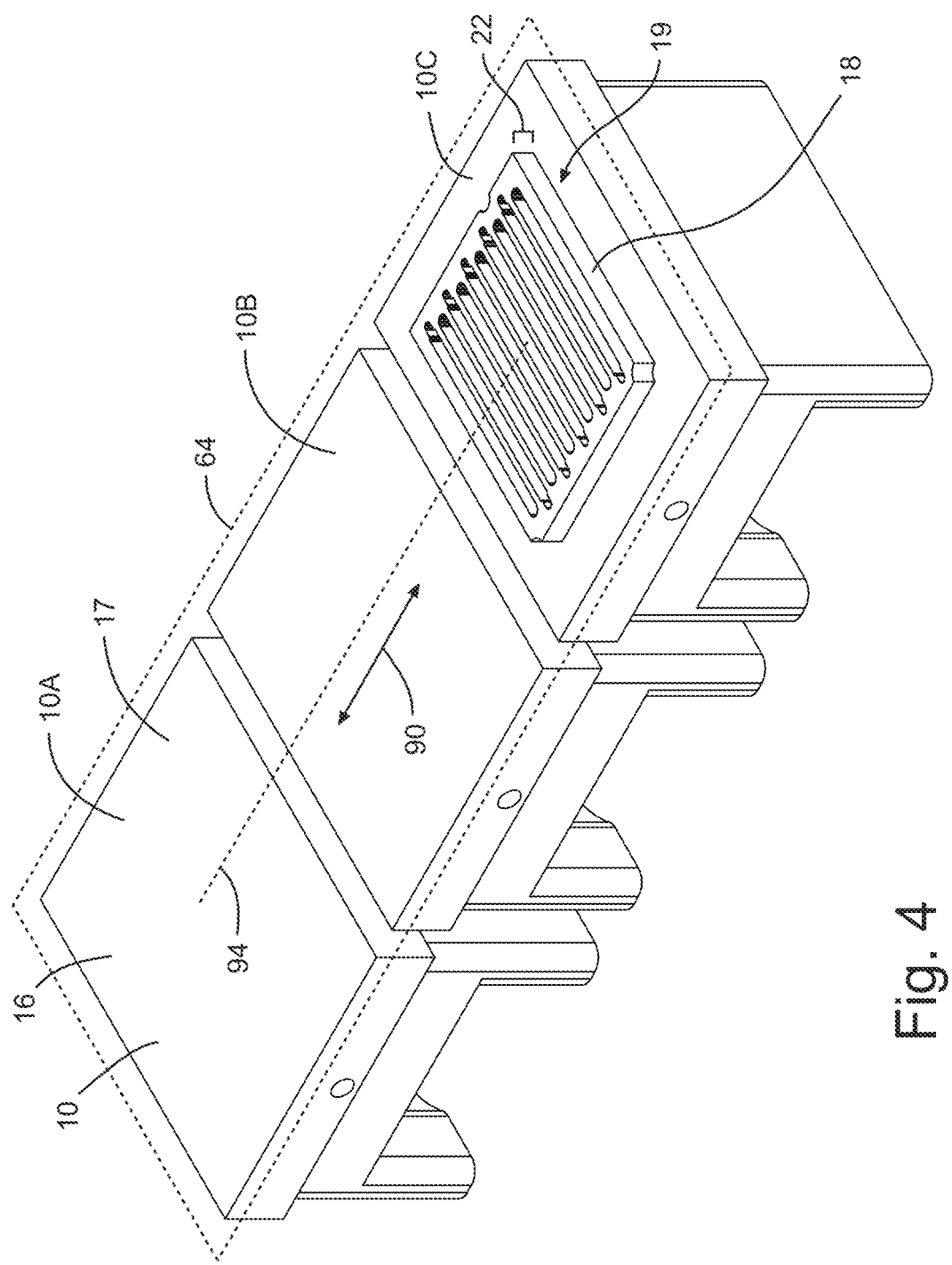
FIG. 4 is a perspective view of a simplified hot block stage assembly. The assembly may comprise multiple hot blocks 10, for example blocks 10A-10C. The blocks may be set to different temperatures and the temperature of cassette 18 may be rapidly changed by moving it from one block 10 to a block 10 at a different temperature.

Referring to FIG. 4 a thermal cycler may include a series of blocks, for example a series of hot blocks 10, in combination with a movable PCR reaction vessel, for example a PCR cassette 18. The cassette 18 may be held in close thermal contact with each hot block 10 in turn, to affect the rapid, accurate and uniform heating and cooling required for effective PCR thermal cycling. A hot block 10 of the series of hot blocks 10 is shown in FIGS. 1A-1C and a corresponding cassette 18 in FIGS. 2A-2D. The hot block 10 may be made of a high thermal conductivity material and may have relatively large thermal mass compared to the cassette 18. Referring to FIGS. 1B and 3A, a temperature sensor 12 (FIG. 1B) may be placed inside the block 10 close to a surface, for example a top surface (heat transfer surface 16) of the hot block 10, that mates with the cassette 18. Referring to FIGS. 3A-D, the PCR cassette 18 may be made of a high thermal conductivity material, and may have a relatively low thermal mass compared to the hot block 10. A view of the cassette 18 seated central to a hot block face is shown in FIGS. 3A-3D. The size and shape of mating surfaces 88 of the hot block 10 and cassette 18 may be designed to have a large surface area and give good thermal contact between the block 10 and the cassette 18 so that the cassette 18 and block 10 temperatures will rapidly equalize when the cassette 18 is moved onto the block 10. To carry out the thermal cycling, several hot blocks 10 may each be controlled to a temperature selected to be close to one of the target PCR step temperatures. During use, the PCR reaction cassette 18 may contain DNA, PCR reagents, and PCR enzymes.

Referring to FIG. 4, block 10 may be one of a series of blocks. Each block 10 of the series of blocks 10 may define a respective heat transfer surface 16, in which the series of blocks 10 define a sequence of positions along a path 94, with each position defined by a respective heat transfer surface 16 of a respective block 10. Each heat transfer surface 16 may be defined by an external face 17, for example a top face as shown, of the respective block 10. Each block 10 in the series of blocks 10 may be spaced from adjacent blocks 10 and/or may be thermally isolated from one another, in some cases forming portions of a larger block. The series of blocks 10 may have two, three, or more, hot blocks 10, for example hot blocks 10A-10C. The series of blocks 10 may be arranged in a row as shown in FIG. 4. Block 10 may form a series of adjacent but thermally isolated preheated hot blocks 10. The PCR cassette 18 may be slid back and forth, for example in directions 90 and/or laterally, across a common plane 64 of the surfaces of the hot blocks 10A-10C, for example respective top surfaces or heat transfer surfaces 16, but may remain in good thermal contact due to the large mating surface area compared to the thickness, for example thickness 22, of the cassette 18.

Referring to FIG. 4, thermal cycling may be accomplished by moving the PCR cassette 18 in a timed sequence across the various surfaces 16 in the desired thermal order. PCR reaction cassette 18 may move along the path 94 into and out of each respective position in the sequence of positions according to a schedule, in which, at each respective position the PCR reaction vessel is in thermal contact with the respective heat transfer surface 16 to equilibrate a temperature of the PCR reaction cassette 18 to a target temperature that corresponds to a respective heating stage in the PCR process. In each respective position, a base heat transfer surface 19 of the PCR reaction cassette 18 may be in thermal contact with, for example sit on and above, the respective heat transfer surface 16, which faces up. The time spent moving between adjacent hot blocks 10A-10C may be short with respect to the thermal response time of the mated cassette 18. The time spent moving may be short in relation to the holding time at each stage. Once at an intended position, the motion may be temporarily arrested and natural thermal equalization may slew the cassette 18 and the hot block 10 to a common temperature in short order due to the intimate thermal contact.

Figure 8:
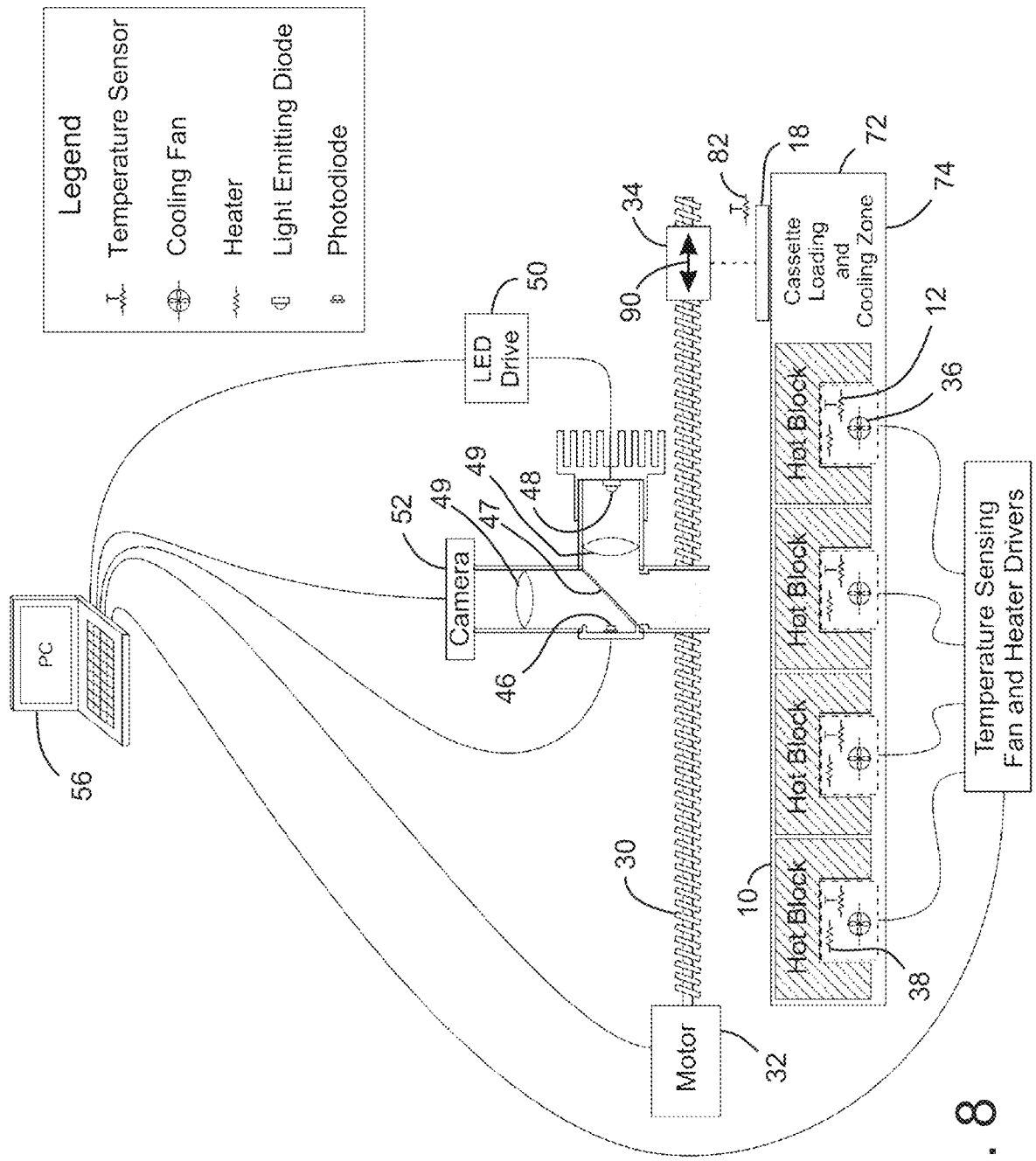
FIG. 8 is a block diagram illustrating a four block PCR sequencer system with melt curve measurement camera features. The four block PCR sequencer system may have heater blocks 10; cassette loading and cooling zone 74; temperature sensors 12, internal heaters (respective heating systems 38), fans 36, and control electronics for control of the temperatures of the heater blocks 10; a positioning system comprising motor 32, lead screw 30, a positioner or cassette carrier 34, and control electronics; an epifluorescence assembly or camera system comprising a camera 52, a dichroic mirror 47, an LED 48, LED drive circuitry 50, a photodiode 46, filters, and other optics such as lenses 49; a viewing mirror 51 (not shown) and a computer 56 providing overall control of the system and data collection.

Referring to FIGS. 4 and 8, the physical motion of the cassette 18 may be coordinated with the temperature control settings on each hot block 10. The series of blocks 10 may be pre-heated to respective temperatures that correspond to different respective heating stages in a PCR process, for example prior to the PCR reaction cassette 18 moving into thermal contact with a respective heat transfer surface. Each hot block 10 may be primed in turn to a slightly pre-biased temperature (with respect to the target temperature for that block's thermal cycle function) in anticipation of the next arrival of the PCR cassette 18. The pre-bias temperature set point may be selected based on the known thermal masses of the hot block 10 and the PCR cassette 18 and the expected temperature of the inbound cassette 18 relative to the target temperature for the next thermal cycling step. As the cassette 18 is slid onto the targeted hot block 10, the temperature set point of that hot block 10 may be reverted to the appropriate target temperature, and the temperature of the cassette 18 and hot block 10 may be allowed to equalize so that the pairing arrives at exactly the intended target temperature (with each component approaching the target temperature from opposite directions). Upon making thermal contact with the PCR reaction cassette 18, the respective block 10 that was previously biased above or below the temperature of the respective block may be subsequently maintained at the respective target temperature. With proper pre-bias temperatures and synchronization of the cassette 18 movement and the hot block 10 temperature setting, the mated hot block 10 and the cassette 18 pairing may achieve fast compliance without significant overshoot of the respective target temperature in the case where the respective block is biased above the respective target temperature, and without undershoot of the respective target temperature in the case where the respective block is biased below the respective target temperature.

Referring to FIG. 4, the PCR reaction cassette 18 may be moved between a first position where the PCR reaction cassette 18 is in thermal contact with a first block 10A that equilibrates the PCR reaction vessel at a first target temperature sufficient to denature the DNA, a second position where the PCR reaction cassette 18 is in thermal contact with a second block 10B that equilibrates the PCR reaction vessel at a second target temperature sufficient to anneal primers to denatured DNA, and a third position where the PCR reaction cassette 18 is in thermal contact with a third block 10C that equilibrates the PCR reaction cassette 18 at a third target temperature sufficient to cause polymerized extension of the DNA. More or less hot blocks and heating stages may be used depending on the PCR process invoked. Prior to the PCR reaction cassette 18 moving into thermal contact with a respective heat transfer surface 16, the respective temperature of the respective block 10 may be biased either above or below a respective target temperature that corresponds to the respective heating stage in the PCR process. The respective temperature of the respective block 10 may be biased below the respective target temperature if the PCR reaction cassette 18 has a temperature that is higher than the respective target temperature as the PCR reaction vessel moves into the respective position, or above the respective target temperature if the PCR reaction cassette 18 has a temperature that is lower than the respective target temperature as the PCR reaction vessel moves into the respective position.

Figure 5:
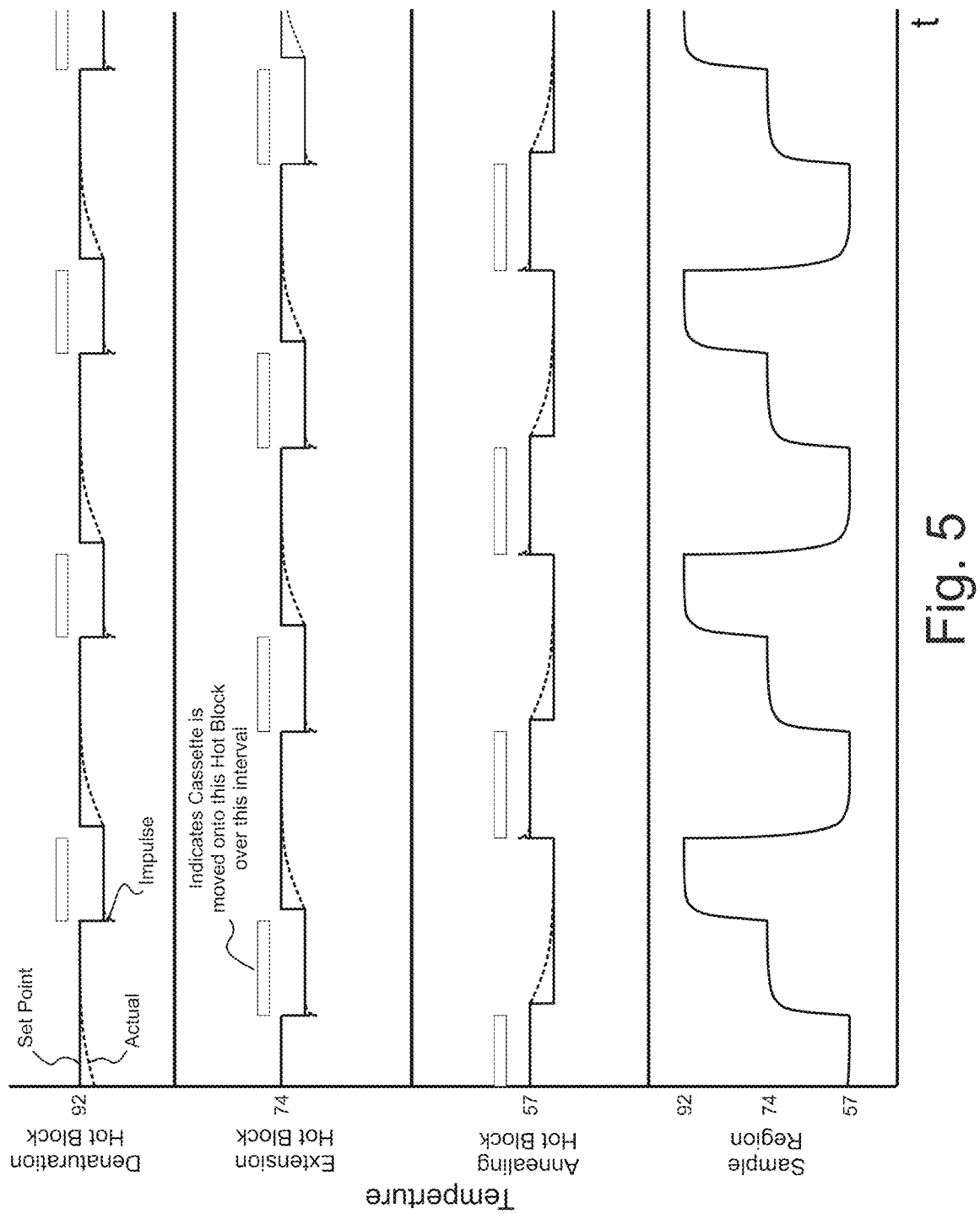
FIG. 5 is a graph illustrating schematic temperature settings and tracking for a three section hot block configuration. The top three sections of this figure show the temperature of the three hot blocks in a three block assembly as a function of time. The temperature set points as well as the actual temperature of the blocks are shown. The grey rectangles above these three sections of the figure show when the cassette 18 is located on the block that the section pertains to. The cassette 18 is first on the Annealing block, then the Extension block, then the Denaturation block, and so on. The bottom section of the figure shows the temperature of the sample in the cassette 18 as a function of time.

FIG. 5 presents a schematic version of the relative timing of the cassette 18 motion, the various set point changes and the responses of each of the hot blocks 10 (one for each of the notional thermal cycling steps) and the temperature response seen in the sample processing regions in the cassette 18. Note that the nominal temperatures shown for each step are selected here for discussion purposes and do not necessarily reflect the exact temperatures of a particular clinical use PCR sequence. This sequencing may allow the hot blocks 10 to simmer near the ideal target temperatures for the various thermal cycling steps such that comparatively little heating or cooling power is needed to shift the block temperature for pre-biasing. The cassette 18 position sequence may be Denaturation—Annealing—Extension. This may repeat for each cycle, with the cassette 18 going from the Extension block 10 at the end of one cycle to the Denaturation block 10 at the beginning of the next cycle.

The top section of FIG. 5 shows the temperature of the Denaturation block 10. When the cassette 18 is not on the Denaturation block 10, the Denaturation block 10 may be set to a temperature slightly higher than the target temperature. The cassette 18 may move onto the Denaturation block 10 from the Extension block 10, which is at a lower temperature. As the cassette 18 moves onto the Denaturation block 10, that block temperature and the cassette 18 temperatures may rapidly equalize, lowering the Denaturation block temperature and raising the cassette 18 temperature to the target temperature with little or no active injection or extraction of heat by the heating system during the equalization period. The set point of the Denaturation block 10 may be changed to the target temperature when the cassette 18 is moved onto the Denaturation block 10 so that the temperature will remain at the target temperature after it quickly arrives there. When the cassette 18 is moved off the Denaturation block 10, the set point may be changed to the pre-bias temperature and the Denaturation block 10 temperature may be comparatively slowly raised back to the pre-bias temperature in anticipation of the cassette's next arrival. Reheating to the pre-bias temperature requires active injection of heat by the control system, which may take advantage of the longer interval available between cassette 18 arrivals to restore the necessary pre-bias.

A similar process happens for the other hot blocks 10. Of note on FIG. 5 is the direction of the step change in each of the hot block 10 temperatures to accomplish the pre-biasing action. For the Denaturation and Extension blocks 10 the pre-bias temperature may be slightly higher than the target temperature because the cassette 18 is coming from a cooler block, whereas for the Annealing block 10 the pre-bias temperature may be slightly lower than the target temperature because the cassette 18 is coming from the hotter Denaturation block 10. The direction of the pre-bias is thus a reflection of whether the cassette 18 is expecting to be heated or cooled. Also of note, in the temperature responses detected at the hot blocks, there may be a slight impulse in the temperature readings very shortly after the cassette 18 arrives. This impulse may manifest from the fact that the cassette 18 extracts (or injects) heat very rapidly from the mating surface of the hot block 10, and this thermal transient passes by the temperature sensors 12 placed near the top surfaces of the hot blocks.

Note that on the time scale of the natural thermal equalization between the hot block 10 and the recently arrived cassette 18, the control loop maintaining the temperature of the hot block 10 does not have to react significantly beyond recognizing that the set point has changed from the pre-bias state to the associated target temperature. After the initial temperature transient when the cassette 18 moves onto the block 10, the temperature may be merely maintained at the target temperature for a dwell period required for that particular PCR step to complete. During this time, the large thermal mass of the heater block 10 combined with the good thermal bond to the cassette 18 help maintain a stable temperature.

Referring to FIG. 8, the individual hot blocks 10 may be temperature controlled by one or more of active heating, resting and active cooling, for example via ON/OFF (bang-bang) control, proportional control, buck control (wherein either a constant cooling or heating source is combined with a variable but complimentary sense heating or cooling source) or any of the other commonly used techniques for temperature regulation. Heat may be easily supplied to the blocks 10 by a suitable mechanism, such as resistive, semiconductor or infrared heating elements, for example heater 38, and active cooling may be carried out by one or more of natural or enhanced natural convection (for instance, using fin arrays or inter coolers), with forced air by a cooling fan 36, by semiconductor cooling, or using circulating liquids or the like.

The hot blocks 10 may be made from a high thermal conductivity, high thermal capacity material, for example (but not exclusively) steel, iron, aluminum, brass or copper. Aluminum may be used due to its ready availability and ease of machining. With respect to physically positioning and supporting the hot blocks 10 relative to each other, care may be taken to limit thermal cross coupling between them and the environment and between each other, so that their respective temperature control issues are simplified. Higher thermal conductivity provides for faster settling time since the thermal energy stored in each of the two mating masses notionally transfers easier. The higher thermal capacity (or more properly higher specific and volumetric heat capacities) allow for more heat to be stored physically closer to the interface surface, which because it is closer also provides for faster settling time (and incidentally smaller physical assemblies). Typical thermal conductivity values for common metals in W/(m·° K) that is {watts per (meter×degree Kelvin)} range from several 10's to several hundreds (things like silver, copper, brass and aluminum are in the mid hundreds while things like irons and steels are in the high 10's). In some embodiments the materials used are at a minimum of around 10 W/(m·° K) thermal conductivity.

The design choices for block 10 and cassette 18 materials in terms of their ability to store heat are more complex than when considering design choices around conductivity, depending upon whether mass units or volumetric units are used. Typical mass based units are kJ/(kg·° K) that is {kilojoules per (kilogram×degree Kelvin)} which is a more conventional use of the notion of specific heat. For instance, ordinary iron has a value of about 0.5 while aluminum has about 0.9. For heat storage in some embodiments, volume also may play a role in the storage and response time because "bigger" tends to also imply "further apart", which in turn impacts heat conduction. Tables for heat capacity of materials are also available in terms of energy density in units such as kJ/(m^3·° K) that is {kilojoules per (cubic meter×degree Kelvin)}. In those units, ordinary iron comes in with a heat capacity value of about 3900 whereas aluminum is around 2500. Several of the relatively higher thermal conductivity materials that also scored high on their volumetric heat storage capacity are potential candidates for both the blocks 10 and cassette 18. Furthermore, aluminum, iron, steel, copper and brass alloys are convenient options as well as such are typically available at common fabrication in machine shops. Aluminum is an effective material by reason of being cheap, easy to machine and having reasonably good thermal performance in addition to being relatively chemically inert which avoids interference with the PCR biochemistry. However, aluminum is not necessarily the optimal design choice. In some cases suitable materials may have either a minimum of 0.2 specific heat capacity at 25° C. in kJ/(kg·° K) (mass units), or in some cases a minimum of 1000 heat capacity in (kJ/m^3·° K) (volume units).

Although not intended as a limitation to the disclosure being described, it is useful to give a sense of the physical scale tested in the prototype versions of this disclosure. Referring to FIGS. 2A-2D, the cassette 18 may be approximately 31 mm wide by 39 mm long and 3.1 mm thick, and may be structured to hold approximately 50 tests (5 in each of the 10 channels 26). Aluminum versions of this cassette 18 may be 6.15 g empty and 7.8 g loaded with hydrated reagent, DNA sample material and a small amount of sealing wax. Referring to FIGS. 1A-1C and 8, block 10 may be made of conductive metal, for example sculpted aluminum. Sculpted aluminum hot block shapes may have a mass of roughly 145 g and the tightly bonded aluminum cased resistive heaters, for example heaters 38 (FIG. 8), may add another roughly 5 g. The topmost rectangular solid section of the hot block 10 may be 57 mm×47 mm×19 mm thick and may account for 85% of the mass of the hot block 10. In some cases, one or more blocks 10 and the PCR reaction cassette 18 are made of the same material.

Figure 20A:
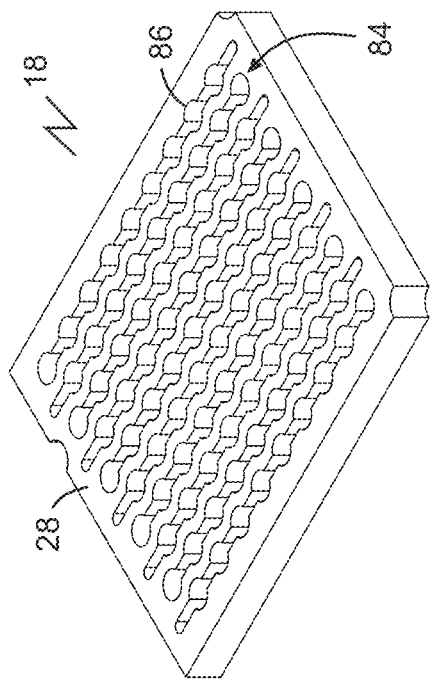
FIG. 20A is a perspective view of another embodiment of a PCR cassette with a series of wells along each sample channel in which each well can be used to introduce different PCR reaction reagents.
Figure 20B:
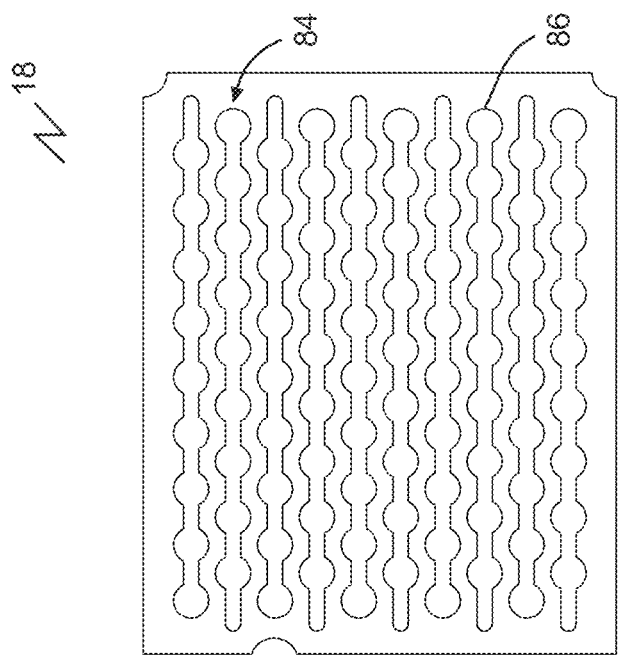
FIG. 20B is a top plan of the PCR cassette of 20A.

Referring to FIGS. 2A-2D, the PCR vessel (cassette 18) may be made from a high thermal conductivity material (for instance a metal such as aluminum) and may be shaped in such a way as to provide enhanced thermal contact and conduction into sample processing regions 20. Referring to FIG. 3A, such functionality may be accomplished by constructing the cassette 18 so that it is comparatively thin, for example having a thickness 22 in a direction normal to the hot block mating surface (that is, thin thermally to allow heat to propagate rapidly though the thickness direction, thin relative to a width and length of the cassette 18, which forms a plate), for example a normal direction 92. In some cases the cassette 18 includes conductive heat fins or walls 24 positioned amongst the sample regions 20 to effect higher heat transfer. Referring to FIGS. 3A and 2D, walls 24 may define long channels 26 that provide increased surface contact area to the PCR process materials and also high conductivity paths for the heat to flow to and from a mating surface 57 of cassette 18 with the hot block 10. Referring to FIGS. 20A-20B, cassette 18 may have other geometries that may provide similar heat transfer features. Cassette 18 may incorporate sinuous channels, arrays of discrete or interconnected wells 86, or other suitable patterns. The channels 26 and wells 84 may be left open at a top 28 so that the reactants, process materials, reaction progress and reaction products may be loaded and subsequently observed during processing and analysis using conventional illumination and image capture techniques. The PCR working volumes may be covered by a thin layer of oil or wax to help suppress evaporation of the reagent and sample mixture. Cassette 18 may have a thin transparent film or laminating layer applied to help encapsulate the sample regions.

The pre-bias heating technique may take advantage of several related and in cases competing thermal effects to quickly draw heat in and out of the cassette 18, without simultaneously introducing undesirable hot or cold spots in the cassette 18 that might alter or even outright corrupt the localized behaviour of the PCR.

The first observation is that in an adiabatic approximation, the combined temperature of the hot block 10 and cassette 18 may reach an equilibrium value after they have been in contact for a period of time, and the equilibrium temperature may be a function of the cassette 18 and hot block 10 thermal masses and their initial temperatures before they came into contact. This rationale may be based on the total system energy before and after the two pieces come in contact.

In some cases the magnitude of bias is selected to minimize the amount of time it takes the PCR reaction vessel to reach the respective target temperature after thermal contact with the respective block. In this disclosure, the magnitude of any over or undershoot in the temperature of the combined thermal masses when using the pre-bias operation may depend in part on the initial accuracy or knowledge of the two incoming temperatures and on the accuracy or knowledge of the relative thermal masses. In practice the thermal mass of the hot block 10 may be well known and may not change during operation. The cassette 18 may be subject to some larger relative variations because it is loaded with samples, reagents and other materials such as encapsulating wax or oil, that are not always placed in the same amounts in every location on every cassette 18. The errors these differences might introduce may be mitigated to some extent by the cassette 18 itself, since in the implementations discussed herein; the cassette 18 may have a significant thermal mass of its own which is easily controlled to good accuracy. The thermal mass of the cassette 18 may dominate the thermal mass of the contents, and the disclosure may make use of this to improve the reliability of the pre-bias settings. To some extent this then may imply that the cassette 18 has a significant mass, and thus so may the hot block 10 by whatever ratio is determined during the design of the instrument.

From this perspective, the required pre-biasing may be very predictable because the thermal capacities and other factors affecting the equilibrium temperature are generally fairly well controlled and mostly known in advance.

The second group of observations are that the rate that heat flows between the hot block 10 and the cassette 18, and to a large degree how the local temperatures in the cassette 18 will evolve before equilibrium is reached, may be determined by several factors including the thermal mating quality between the cassette 18 and hot block 10, by the relative thermal conductivities of the masses and by the mechanical geometries used to store and conduct the heat.

For example, local variations in the thermal contact resistance between the block 10 and the cassette 18 may translate into lags and gradients in the temperature in the PCR region. Using high thermal conductivity material for the cassette 18 and ensuring that the internal structure of the cassette 18 tends to evenly distribute the heat may help smooth out local temperature variations and make the PCR more consistent across the cassette 18. This may imply that the cassette 18 will have a non-trivial mass since effecting good heat spreading requires non-trivial amounts of material to conduct the heat.

Referring to FIG. 3a, another consideration is that the hot block 10 itself may present a substantially isothermal surface to the mating cassette 18 (both during the cassette 18 transitions onto and off the hot block 10 and while the cassette 18 is resident on the hot block 10), so that heat would flow into or out of the cassette 18 in a substantially normal direction, for example direction 92, to top surface 16 of the hot block 10 (notionally so that the PCR regions are all exposed to the same temperature cycling history). Such an isothermal behaviour requirement may be solved by making the hot block 10 comparatively thick in comparison to the cassette 18 so that the block 10 plays the dominate role shaping the temperature profiles that might exist when the cassette 18 arrives. Also, providing a buffer zone that projects out past the final landing area reserved for the cassette 18 may help reduce the production and communication of thermal transients that might be induced in the initial mating surface region of the hot block 10 as the cassette 18 arrives from one side. Such a buffer zone may help supply the thermal load brought by the cassette 18 as it arrives and may provide a path to carry and homogenize heat in the hot block 10, but may come at the price of added material. For example, if the hot block 10 is thin or thermally light, the incoming cassette 18 will distort the spatial temperature profile within the block 10 as the cassette 18 begins to absorb or reject heat while it sweeps into position, which in turn impacts the subsequent heat flow and temperature stabilization provided by the hot block 10 when the cassette 18 finally stops in place. If the block 10 is "thick", these problems may be reduced.

Another heat flow issue that may be considered is the ratio of the thermal mass of the cassette 18 and the hot block 10. If the ratio is low, that is the cassette 18 is comparatively light, then the hot block 10 may dominate the heat flow, the pre-bias may be negligible and the hot block 10 may be set to a value near the target temperature for the PCR step. When the cassette 18 arrives, the temperature may shift and settle asymptotically without any over or undershoot with the final accuracy determined mostly by the accuracy of the hot block 10 temperature control. In the other extreme, if the ratio is high, that is the hot block 10 thermal mass is small with respect to the cassette 18, the cassette 18 may dominate and to get any useful heat flow the hot block 10 pre-bias may need to be very large. This situation may generate the highest instantaneous heat flow rates and fastest equilibrium convergence because the initial temperature differences are large and the total thermal mass involved is lower, but this introduces severe transients. As well, if the hot block 10 is small or thin, it may be less likely to act as a isothermal surface to the cassette 18, further aggravating temperature gradients and excursions away from the ideal temperatures through the cassette 18 volume.

Figure 14:
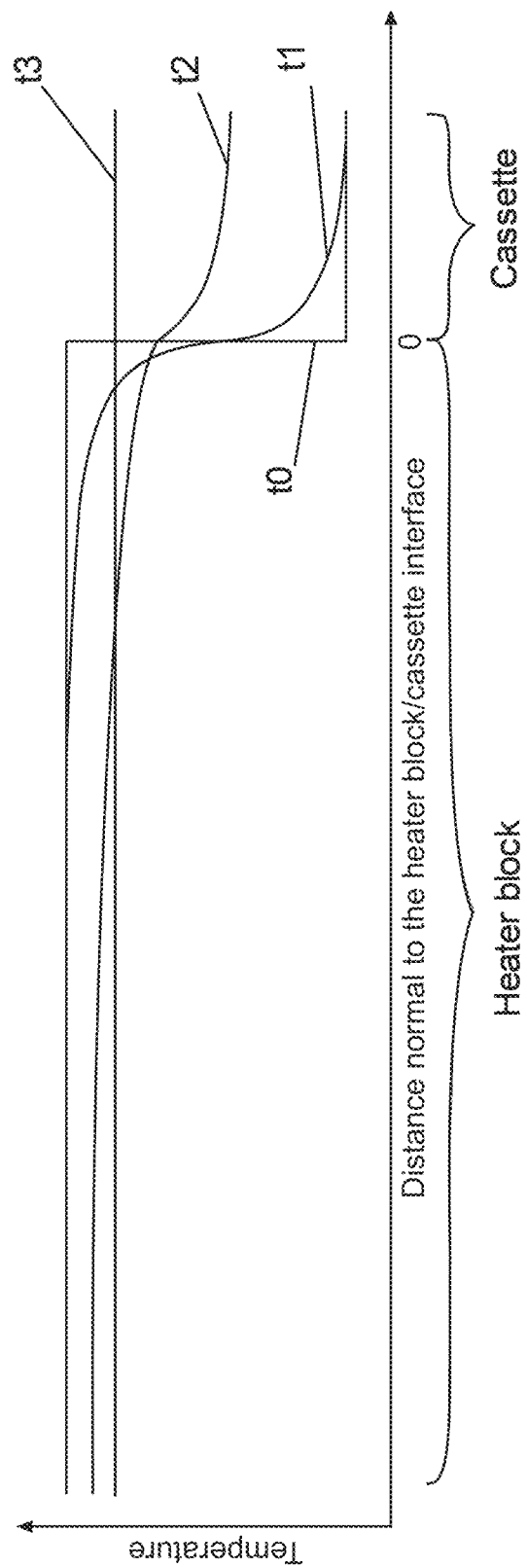
FIG. 14 is a temperature profile in a heater block and cassette immediately after the cassette is moved onto a heater block that is more thermally massive than the cassette. The temperature profile is shown at various times where t0<t1<t2<t3. The cassette and heater block initially come into contact at t0. The temperature has reached its final, equilibrium state at t3. It is assumed for discussion purposes that there is no heat flow to the environment. A one dimensional geometry has been assumed to simplify the discussion.
Figure 15:
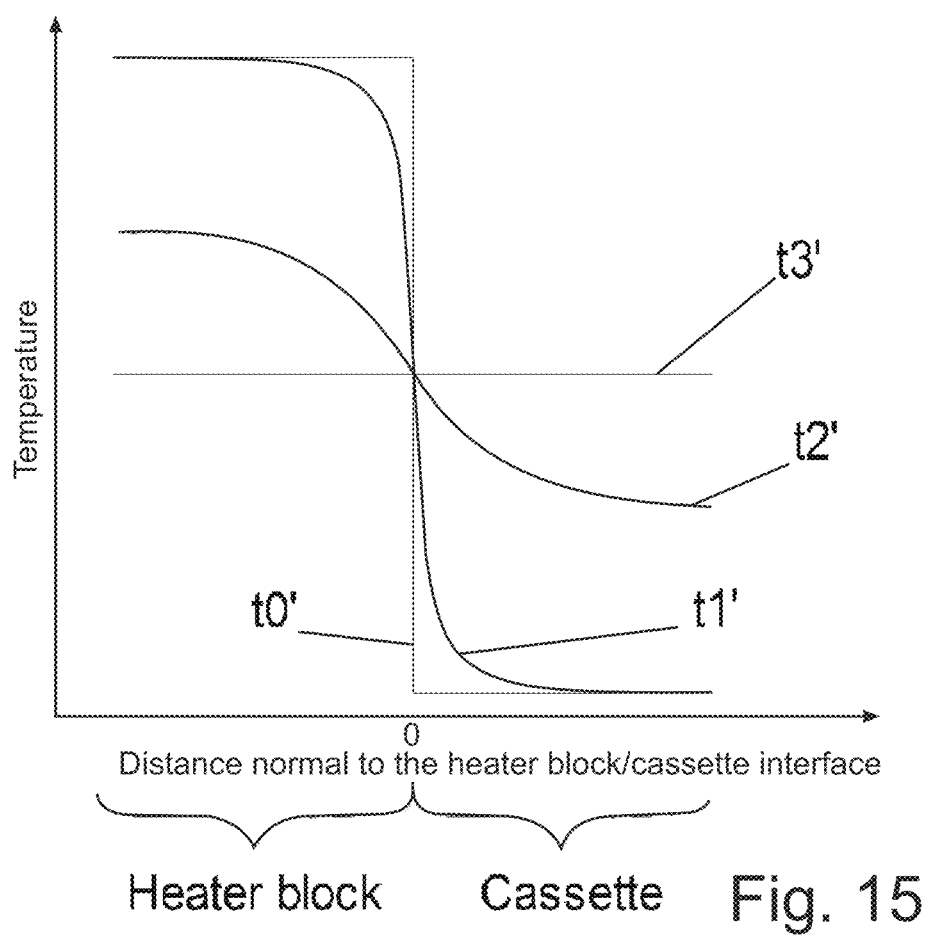
FIG. 15 is a temperature profile in a heater block and cassette immediately after the cassette is moved onto a heater block that is equally thermally massive to the cassette. The temperature profile is shown at various times where t0'<t1'<t2'<t3'. The cassette and heater block initially come into contact at t0'. The temperature has reached its final, equilibrium state at t3'. It is assumed for discussion purposes that there is no heat flow to the environment. A one dimensional geometry has been assumed to simplify the discussion.

FIGS. 14-15 show the thermal profile of a heater block 10 and a cassette 18 at several times after the cassette 18 is placed on the block 10. The three figures show three different heater block 10/cassette 18 thermal mass ratios. In each case, the cassette 18 thermal mass is kept constant, but the heater block 10 mass is altered. The geometry has been simplified to one dimension. There is no heat flow to/from the environment. The initial temperature of the cassette 18 and the final equilibrium temperature is the same in each case and the initial cassette 18 temperature is lower than the initial heater block 10 temperature. The initial temperature of the heater block 10 that is required to reach the desired equilibrium temperature depends on the mass of the heater block 10. A smaller mass heater block 10 notionally requires a higher initial pre-bias temperature than would a more massive heater block 10.

FIG. 14 shows the case where the heater block 10 has a greater thermal mass than the cassette 18. The heater block 10 and the cassette 18 are brought into contact at time to. The heater block 10 initially has a temperature slightly higher than the equilibrium temperature while the cassette 18 is cooler than the equilibrium temperature. The difference between the equilibrium temperature and the heater block 10 initial temperature is less than the difference between the equilibrium temperature and the cassette 18 initial temperature. When the block 10 and the cassette 18 are brought into contact, the temperature at the interface rapidly reaches the midpoint between the two initial temperatures (assuming they are constructed of the same material and are in good contact), which is lower than the equilibrium temperature. Heat flows from the heater block 10 to the cassette 18, lowering the heater block 10 temperature and raising the cassette 18 temperature. The temperature changes are greatest near the heater block 10/cassette 18 interface initially, but the temperature profile flattens out over time until and equilibrium is reached. The equilibrium temperature is closer to the initial heater block 10 temperature than the initial cassette 18 temperature.

FIG. 15 shows the case where the heater block 10 has the same thermal mass as the cassette 18. The heater block 10 and the cassette 18 initial temperatures are equally distant from the equilibrium temperature—the initial heater block 10 temperature being higher. When the block 10 and cassette 18 are brought into contact, the temperature at the interface may quickly reach the midpoint between the two initial temperatures. Heat flows from the heater block 10 to the cassette 18, lowering the heater block 10 temperature and raising the cassette 18 temperature. The temperature changes may be greatest near the heater block 10/cassette 18 interface initially, but the temperature profile flattens out over time until and equilibrium is reached. The equilibrium temperature is midway between the initial heater block 10 temperature and the initial cassette 18 temperature. The temperature gradient at the heater block 10/cassette 18 interface shortly after t0' is may be larger than it is for FIG. 14 shortly after t0. As a result, heat may actually initially flow into the cassette 18 more quickly in the case of FIG. 15 than in that for FIG. 14 because in the case of FIG. 14 the initial block 10 and cassette 18 temperature difference would be lower to produce the same equilibrium temperature.

Figure 16:
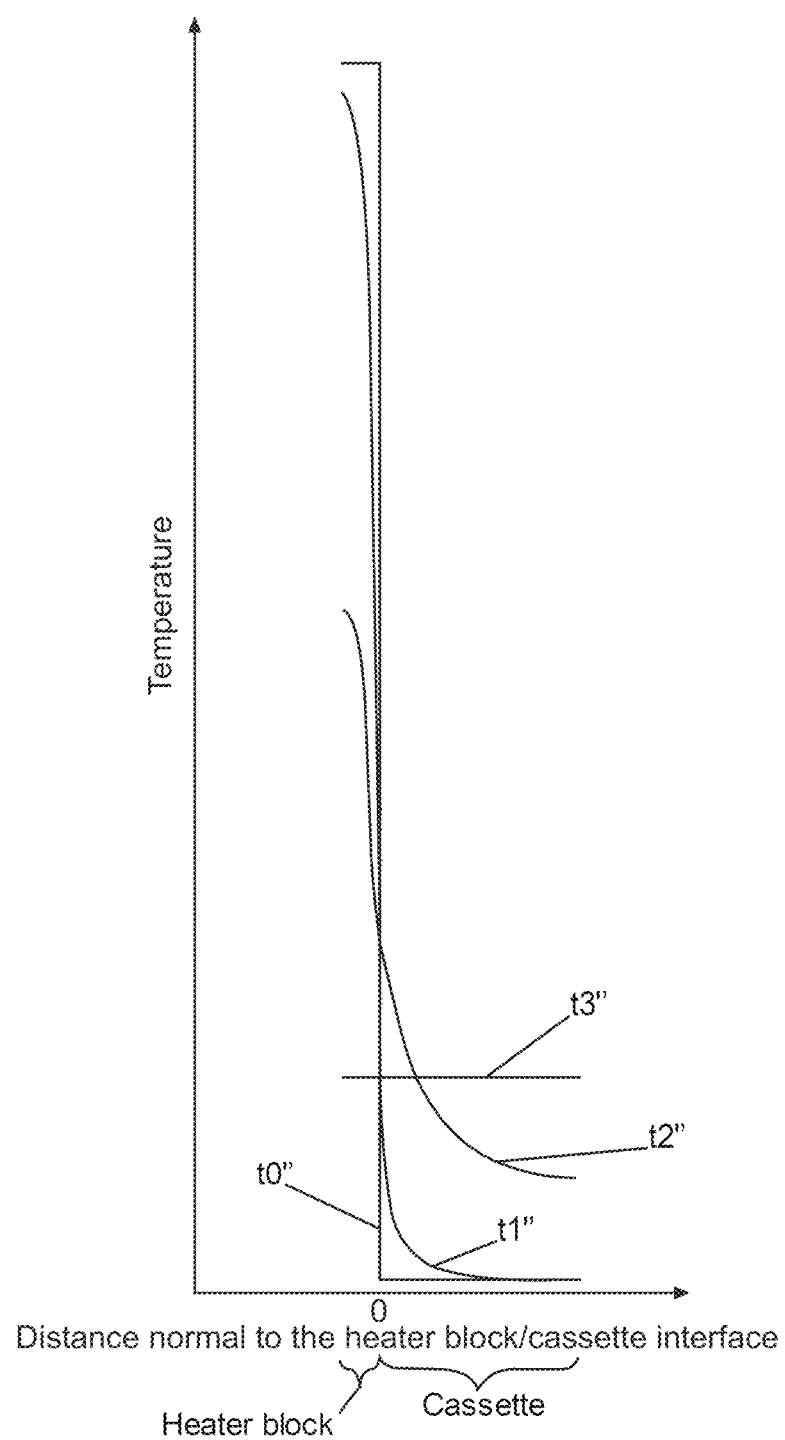
FIG. 16 is a temperature profile in a heater block and PCR cassette immediately after the cassette is moved onto a heater block that is less thermally massive than the cassette. The temperature profile is shown at various times where t0"<t1"<t2"<t3". The cassette and heater block initially come into contact at t0". The temperature has reached its final, equilibrium state at t3'. It is assumed for discussion purposes that there is no heat flow to the environment. A one dimensional geometry has been assumed to simplify the discussion.

FIG. 16 shows the case where the heater block 10 has less thermal mass than the cassette 18. The heater block 10 and cassette 18 are brought into contact at time t0". The heater block 10 may initially have a temperature much higher than the equilibrium temperature while the cassette 18 may be cooler than the equilibrium temperature. The difference between the equilibrium temperature and the heater block 10 initial temperature may be greater than the difference between the equilibrium temperature and the cassette 18 initial temperature. When the blocks are brought into contact, the temperature at the interface may quickly reach the midpoint between the two initial temperatures, which is higher than the equilibrium temperature. Heat may flow from the heater block 10 to the cassette 18, lowering the heater block 10 temperature and raising the cassette 18 temperature. The temperature changes may be greatest near the heater block 10/cassette 18 interface initially, but the temperature profile flattens out over time until and equilibrium is reached. The equilibrium temperature may be closer to the initial cassette 18 temperature than the initial heater block 10 temperature. The temperature gradient at the heater block 10/cassette 18 interface shortly after the heater block 10 and cassette 18 are brought into contact may be the largest of the three cases (FIGS. 14-16), so heat flow may flow into the cassette 18 more quickly.

Figure 18:
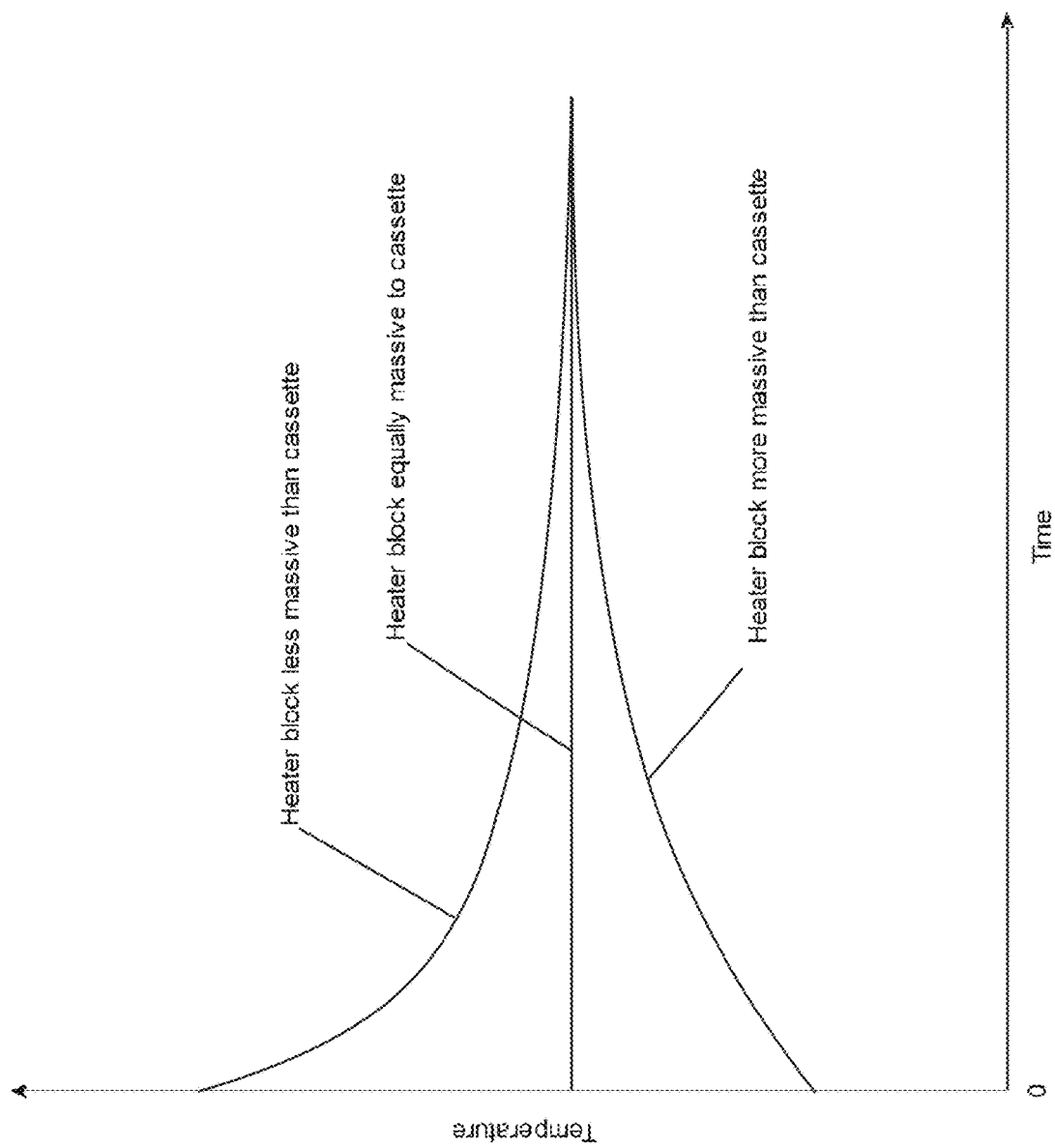
FIG. 18 is a graph illustrating temperature at a heater block/PCR cassette interface after the cassette is placed on the block. Three different heater block to cassette thermal mass ratios are shown. Perfect thermal contact between the block and cassette is assumed.

FIG. 18 shows the temperature at the heater block 10/cassette 18 interface as a function of time for the three cases addressed in FIGS. 14-16. The temperature may be initially above the equilibrium temperature for the small block 10 and may be below the equilibrium for the large block 10. The same equilibrium temperature may be reached in all cases.

Figure 19:
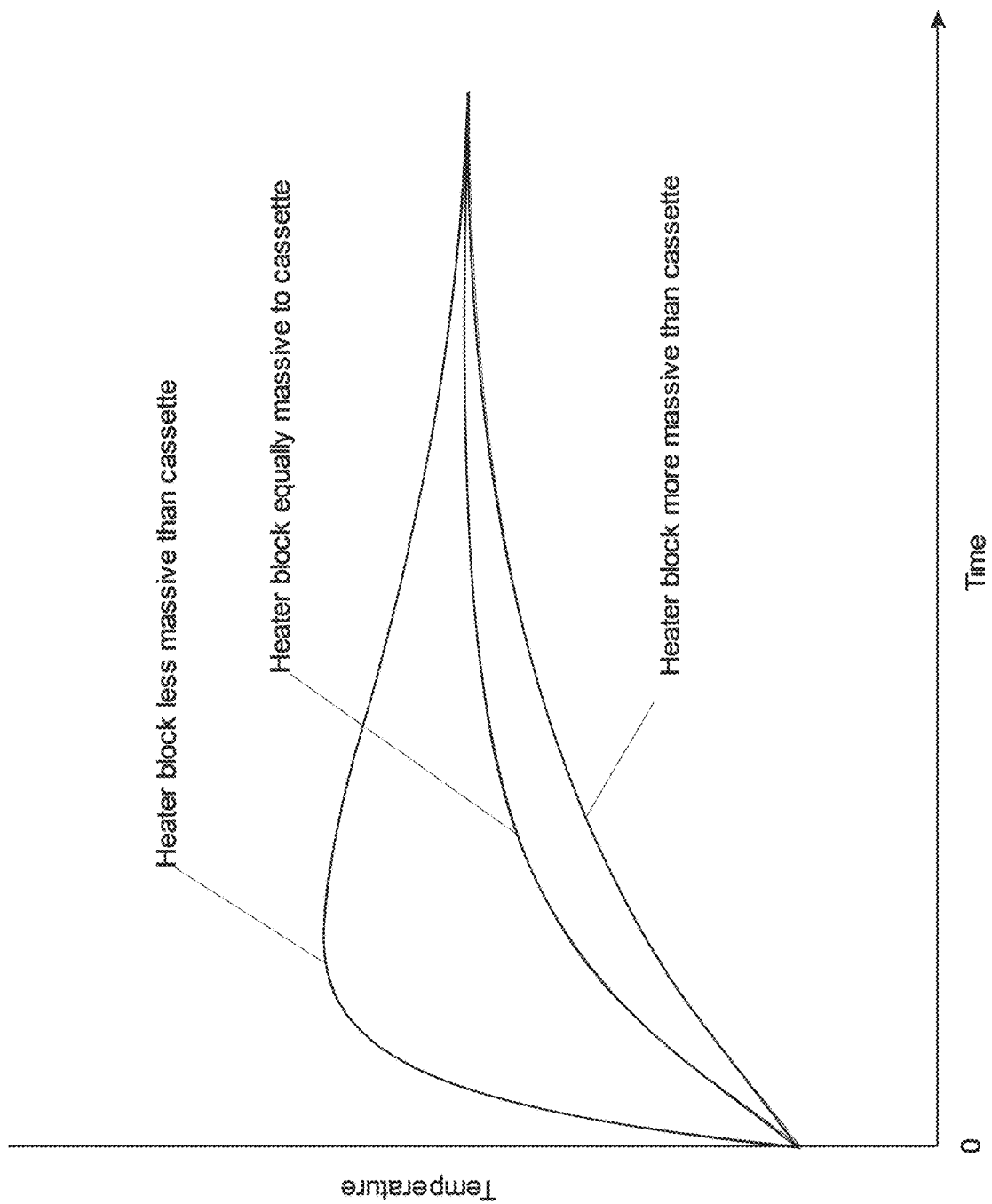
FIG. 19 is a graph illustrating temperature inside a PCR cassette very close to a heater block/PCR cassette interface after the cassette is placed on the block. Three different heater block to cassette thermal mass ratios are shown. Perfect thermal contact between the block and cassette is assumed.

FIG. 19 shows a plot of the temperature inside the cassette 18, but very near to the heater block 10/cassette 18 interface for the three cases. In all three cases, the temperature may start at the same cassette 18 initial temperature. For the small heater block 10 the temperature may over shoot the equilibrium temperature and then drops down to the equilibrium temperature. If the block 10 is the same size as the cassette 18, the temperature may rise up to the equilibrium temperature, but never over shoots. If the block 10 is larger than the cassette 18, the temperature may rise more slowly than the other two cases and is always less than or equal to the temperature in those cases. The amount of overshoot mitigates as the heat surge propagates deeper into the cassette 18 since the thermal resistance and thermal mass of the material in the cassette 18 act as a low pass filter. Subsequently the overshoot seen at the PCR sample location may be lower in amplitude.

For a given cassette 18 design, and anticipating the use of the pre-bias technique presented herein, there may be an optimal thermal mass ratio concept in play that may drive the design of the hot block 10 and that may provide for an optimal cassette 18 rate of temperature change with respect to settling time, temperature accuracy and acceptable transient behaviour. The final selection of the hot block size, shape and material may thus be a compromise between getting rapid heating or cooling of the cassette 18, having an effective isothermal surface to couple the cassette 18 and block 10, preventing temperature overshoot in the cassette 18, observing practical limitations on the peak sample region temperatures and keeping in mind the available heating or cooling power necessary to slew the hot blocks 10 in time for the next cassette arrival. More specifically, choosing a hot block 10 with a very large or very small thermal mass with respect to the cassette 18 may not achieve the best application level performance. Thus, there may be a range of good typical thermal mass ratios to consider, the ultimate choice for an application being implementation specific.

Regarding the relative sizing of the thermal masses for the prototype system discussed herein, the thermal mass ratios may be chosen to lie in the range of between 15:1 and 35:1, for example 25:1 (hot block 10 to vessel or cassette 18), which may simultaneously provide for storing a significant amount of heat energy in the hot block 10 relative to the cassette 18, allows for sufficient material to effect a good isothermal mating surface on the hot block 10, but keeps the overall mass low enough that the hot block 10 temperatures can be slewed both from start up as well as while simmering at the pre-bias points using acceptable heating and cooling power and energy and operating within in a time frame suitable for the intended PCR applications. However, it may be reasonable to expect that in other implementations using one or more features of this disclosure, thermal mass ratios as low as 1:1 or as high as 100:1 may be preferred, with the expectation that evolving the technology toward the 1:1 end of the spectrum would be the natural course for reducing overall system size.

The discussion of the optimal thermal mass ratios and how to effectively use the pre-biasing assumes that in a practical implementation of this disclosure that the thermal masses of the cassette 18, PCR reagents and sample cannot be made trivially small compared to the thermal mass of the hot block 10 which would allow operating in the limiting case where the cassette 18 and contents could heat or cool almost instantly. This could be accomplished by going to either of two extremes cases, that is either by making the hot blocks very large or the PCR vessel and its contents small thermal mass wise. These are not practical in the intended instrument applications where this disclosure would be used, as the hot blocks 10 cannot be made arbitrarily large (which would result in comparatively large and cumbersome blocks requiring large heater and cooler power to operate).

Taking the other limiting case of making the cassette 18 thermally very light may not be readily achievable due to several reasons. Thermally light implies either physically small or made from light materials. Light materials tend to not have the high thermal conductivity required for some embodiments to operate properly. Physically small devices also make sample placement trickier which increases the variability in thermal mass and mass distribution which in turn impacts response time uniformity and consistency. Effective mating to the hot block 10 to get predictable thermal response may be more problematic with small cassettes 18 as they become more susceptible to local mating surface contamination such as dust and debris on the mating faces. Smaller features may exacerbate problems with introduction and treatment of gas bubbles and the effective release of out-gassing which can dislodge sample materials or PCR reagents in the cassette.

Obtaining reasonable sample statistics in a small package may be more difficult as well. Smaller sample volumes may introduce detection reliability issues at very low DNA concentrations because the mean sample volume required to reasonably assume at least "1" offending contaminate entity grows significantly as concentration drops. For example, if the detection requirement is 1 per ml then if the concentrations are actually this low, on average at least 1 ml of sample must be analyzed. This naive example is used to demonstrate the problem, in practice many times this volume may need to be analyzed to have confidence in the results. Thus, although very small sample volumes might enable the use of small PCR vessels, they may become less useful as an analysis tool.

From a practical perspective many clinical applications for this kind of technology may use manual techniques to prepare PCR reagents, incubate and concentrate samples and load the PCR vessels. This may place another constraint on how small the PCR vessels can reasonably be. However, this disclosure does not limit itself to this hand work scale and anticipates being reduced to progressively smaller formats as small scale fabrication and automatic preparation technologies evolve. Shrinking the physical implementation would also likely require development of sample pre-concentration techniques to mitigate reduced sample volumes, or alternately, it may be that applications exist where low detection limits are not necessary.

Also, it may be desirable to be able to accommodate multiple PCR sets in the cassette 18 simultaneously. Each PCR set may comprise a particular sample and reagents. There may be multiple PCRs each having sample from the same source but different reagents, samples from different sources, and control PCRs sets. This may limit how small the cassette 18 can be.

Regarding the materials of construction, as a matter of convenience, selecting the same material for both the hot blocks 10 and the cassettes 18 may allow the operator to more easily anticipate the pre-bias differential temperatures.

As an illustrative example, consider a cassette 18 currently at 70° C. and the next target temperature is 95° C. The difference is simply 25° C., so if the specific heat capacities of the two materials are nearly identical and the mass ratio is about 25:1, then pre-biasing the hot block 10 by 1° C. to 96° C. will allow the hot block 10 to bring the cassette 18 up to 95° C. without needing to add new heat during the initial equalization period, and the hot block 10 can then be set to regulate for exactly 95° C. once the cassette 18 arrives. However, using similar materials is by no means a rule and potentially different base alloys or materials may have advantages in certain implementations of the disclosed embodiments. Also note in this simplified example, the aggregate mass of the cassette 18 includes the sample, reagents and other materials installed in the PCR region of the cassette 18. Such materials may not have the same thermal characteristics as the cassette 18 material, but as the cassette 18 is often (but not exclusively) thermally much larger than the contents, the assumption they are all about the same is useful for first estimate purposes. In a practical implementation, the aggregate mass of a typical loaded cassette 18 may be determined by analysis and operational testing to make certain the pre-bias settings were tuned correctly.

Referring to FIGS. 2A-2D and 20A-20B, one or more channels 26 and/or one or more channels 84 (FIGS. 20A-20B) of the cassette 18 may optionally contain discrete test PCR reagent elements as pre-deposited or pre-loaded forms, including dry reagents held in desiccated gels or bonded or painted on the channel 26 surfaces or as reagents held in a secondary level of containment such as capillary tube sections or paper strips fitted to one or more channels 26 and/or one or more channels 84 (FIGS. 20A-20B). Dry or liquid samples and reagents may be loaded directly into the cassette 18 at the time of use by manual or automated means. Empty or partially loaded cassettes 18 may be fed through an automated dispensing system that incorporates some or all of the salient features of this disclosure to effect PCR thermal cycling.

Referring to FIGS. 2A-2D, the structure of the cassette 18 may be fabricated from a homogeneous material, for example metal formed by traditional machining processes. Cassette 18 may have other constructions such as PCR vessels made according to various lamination processes (for example, but not limited to techniques and constructions drawn from the art of printed circuit board manufacturing where layers of copper, aluminum or other metals are sandwiched in an epoxy glass matrix), through pressure forming, stamping, sintering or molding of metals, or by using composites with good thermal conductivity properties such those containing high amounts of carbon fibre, metallic or ceramic fillers or other similar engineering materials that are or may become available. Cassettes 18 may have any other suitable construction in which the resulting structure and material preserve the essential aspects of a high thermal conductivity and good thermal coupling and can be formed appropriately.

Figure 7:
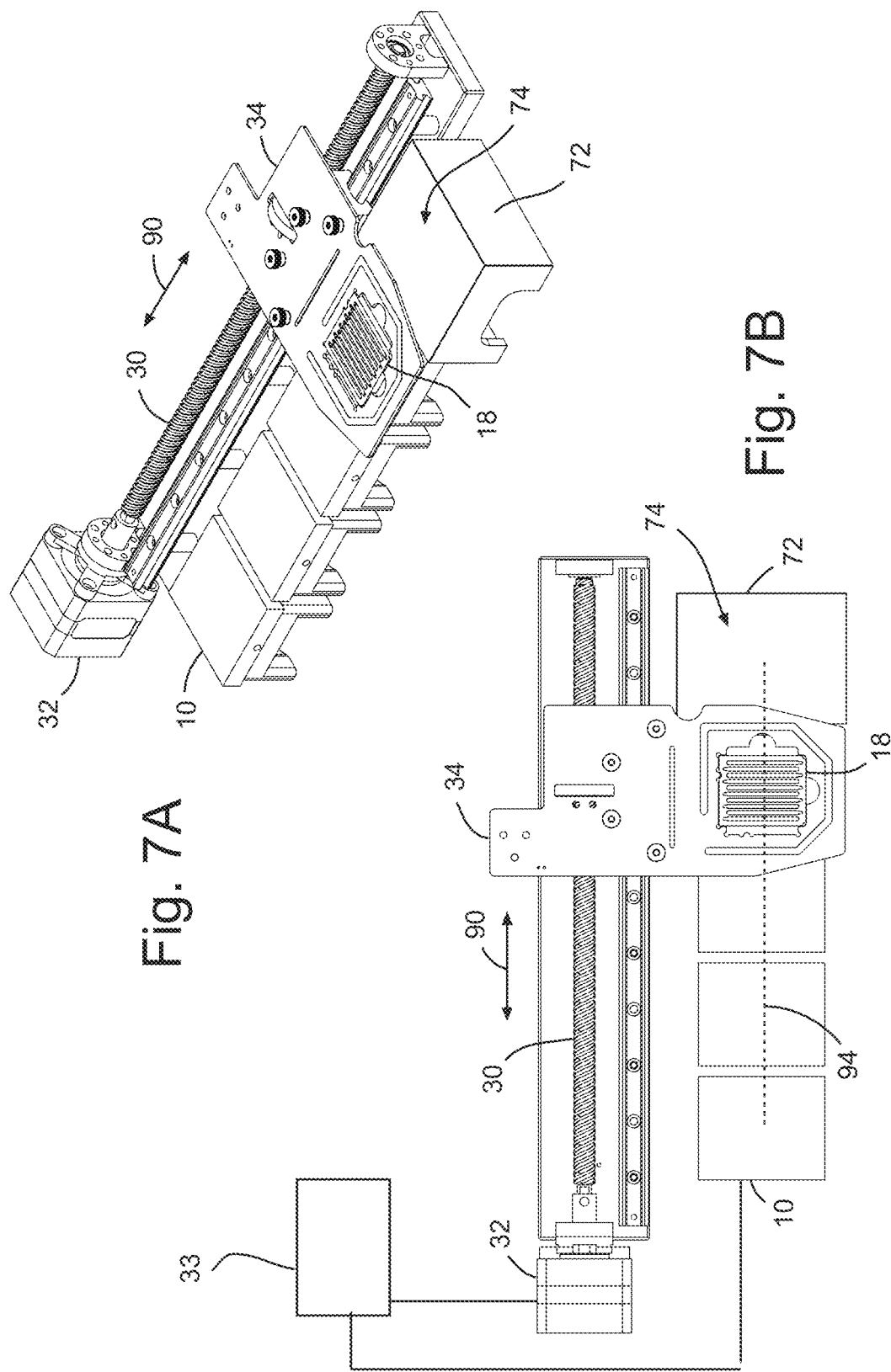
FIG. 7A is a perspective view of a conceptual mechanical layout of a hot block sequencer.
FIG. 7B is a top plan view of a conceptual mechanical layout of a hot block sequencer (thermal cycler). The thermal cycler of FIGS. 7A-B has four heater blocks; an unheated block for cooling at the right-hand side; a lead screw 30, a motor 32, and a cassette carrier 34 for movement of the cassette 18 in directions 90; and cassette 18. A controller 33 may be connected to operate various components of the system, such as the lead screw 30 and the hot blocks 10. In some embodiments, such as shown in FIG. 8, the controller may be an external or externally mounted controller such as a computer 56, and in some embodiments, such as shown in FIG. 10, the controller may be embedded within the structure of the thermal cycler itself.

Referring to FIGS. 7A-7B and 8, the cassette 18 may be moved across the hot blocks 10 via a suitable actuator such as a mechanical lead screw arrangement. Using a lead screw manipulator should not be seen as a limitation of the disclosure as other methods to move the cassette 18 may be used, for example belts, linear motors, chains, or other manipulators commonly used for such purposes. FIGS. 7A-7B and 8, show the use of four hot blocks and an unheated area, unheated end section 72, and/or cassette loading and cooling zone, 74 for loading and unloading of the cassette 18. The unheated end section 72 may be used to rapidly cool cassettes 18, for example so that they are safe to touch. A linear screw actuator may be connected to a controller that has a readable medium that stores the schedule.

Referring to FIG. 7B, a transitional block may be positioned adjacent and prior to a respective position along the path 94. While the PCR reaction cassette 18 is moving toward the respective position, the PCR reaction cassette 18 may be pre-heated or pre-cooled in the direction of a respective target temperature of the respective position by heat transfer across a heat transfer surface of the transitional block as the PCR reaction cassette 18 comes into thermal contact with the transitional block. The respective block 10 at the respective position may be pre-heated to the respective target temperature that corresponds with the respective heating stage. Each block 10 of the series of blocks may be maintained in a pre-heated state when not in contact with the PCR reaction cassette 18.

Referring to FIGS. 7A-7B and 8, the additional transitional hot block 10, relative to the number of hot blocks 10 shown in FIG. 4, may be used in another mechanism available with this disclosure to accelerate heating or cooling rates, but that still provides the advantages of minimal overshoot and accurate target temperature control. Any of the thermal cycling step transitions may be accomplished using two or more blocks 10 that individually operate near the target temperature for the next step but that may have slight but intentional differences in their temperatures as the cassette 18 moves onto or past their working surface. For the purpose of simplifying the discussion of this method, consider here the use of paired hot blocks 10, although more than two blocks may be used for such a purpose. The first of the paired hot blocks that the cassette 18 encounters may be set to a temperature past the intended target temperature ("past" meaning that the set temperature is further from the current cassette 18 temperature than the next intended target temperature, and also that the temperature difference thereto is larger than what would be strictly required to accomplish the pre-biasing technique discussed earlier herein). When the cassette 18 is first brought onto that hot block 10, the cassette 18 temperature may start to slew toward a equalization temperature past the target temperature. As the cassette 18 temperature approaches the target temperature needed for the next PCR step, the cassette 18 may be shuttled onto the adjacent hot block 10 of the pair which may have been established at the exact target temperature. The cassette 18 temperature may then stop slewing abruptly and assuming the timing of the motion was correct, may be sitting exactly at the target temperature. This technique may be possible with the hardware configuration described herein because the thermal characteristics of the loaded cassette 18 may be very consistent and well known. The correct movement timing may be determined empirically with relative ease, but may also be calculated based on the relative thermal characteristics of the hot blocks 10 and the cassette 18. This paired block technique may be particularly useful for transitioning to the annealing temperature step (in which case and for clarity, the first hot block of the pair would be set "cold" to provide accelerated cooling), since there is less risk associated with slightly over cooling the cassette 18 if the timing is not perfect.

Such a technique may allow the cassette 18 to reach the target temperature more quickly than if the first block 10 was set at the pre-bias temperature described previously. With the block 10 at the pre-bias temperature described previously, the block 10 and the cassette 18 may settle toward an equilibrium temperature that is the same as the target temperature. The cassette 18 temperature may approach the equalization temperature asymptotically (it may take a relatively long time). When the first block 10 temperature is set farther from the target temperature than the pre-bias temperature described previously, the cassette 18 temperature may reach the target temperature relatively quickly. Its temperature may still be changing as it reaches the target temperature and may pass the target temperature if it were left on the block 10.

For the transition to the Denaturing step, the dual block setup may also provide a useful benefit. In such a scenario, the preheat block 10 of the pair may be provided with a slight excess in positive pre-bias so that a non-trivial but well controlled slew rate was still available as the cassette 18 neared the high Denaturation target temperature. Once the temperature of the cassette 18 is "just right" the cassette 18 may be repositioned onto the hot block 10 at the target step temperature, for example to achieve faster response but without overshoot.

In another configuration of the dual block setup, both blocks 10 in the pair may be set to exactly the target temperature. With this configuration, there may be a reduced possibility that the cassette 18 temperature may over shoot anywhere in the cassette 18. This may be important if the target temperature was very near the boiling point of the sample or reagents as an example. When the cassette 18 is moved onto the first block 10 of the pair, the temperatures of the first block 10 and the cassette 18 may equalize toward a temperature T3 between the block temperature T1 and the cassette 18 temperature T2. T3 may be relatively close to T1 because the thermal mass of the block is larger than the cassette 18. The cassette 18 may then be moved onto the second block 10 in the pair and the second block 10 and the cassette 18 temperatures may equalize toward a temperature T4 that is between T3 and T1. Since T3 is close to T1, T4 will be very close to T1.

FIG. 8 also indicates a number of additional features that may be included in a practical instrument implementation, including heater control and temperature monitoring, data collection and optical components needed to review PCR progress and carry out melt curve analysis during or at the end of the programmed thermal cycling sequence.

Figure 9A:
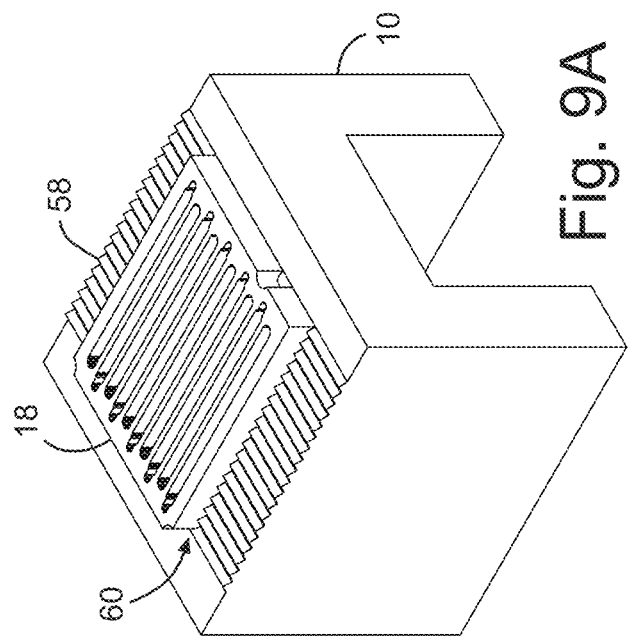
FIG. 9A is a perspective view of a hot block 10 and cassette 18 having respective mating grooved surfaces 58 and 60 that may increase the contact surface area between them.
Figure 9D:
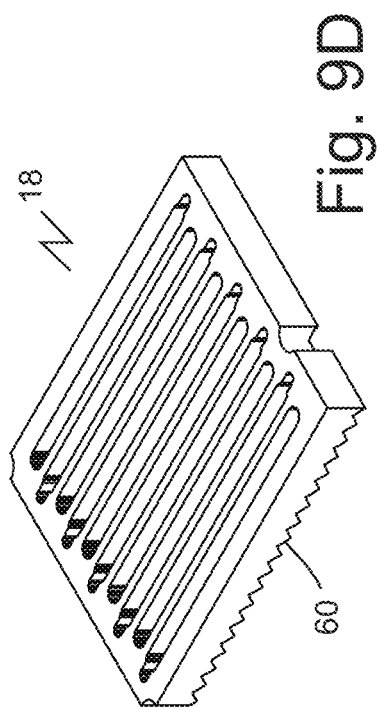
FIGS. 9D-9G show cassette 18 having a grooved mating surface 60.
Figure 9B:
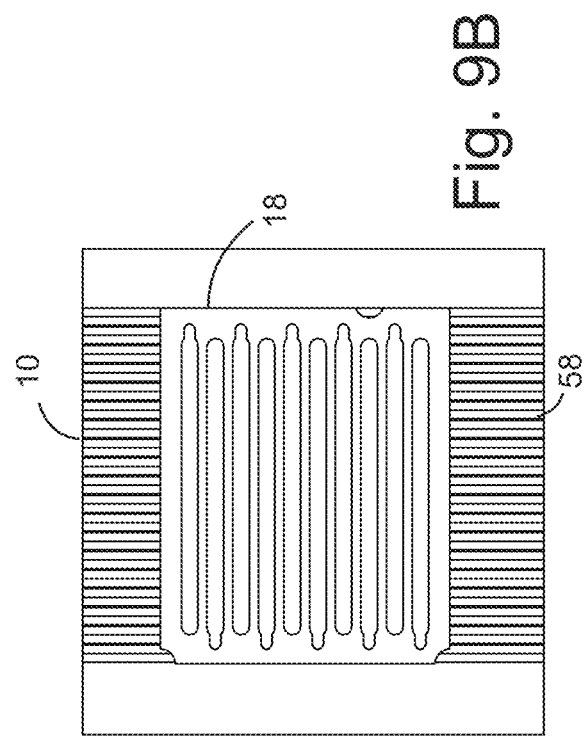
FIG. 9B is a top plan view of the PCR cassette and the hot block of FIG. 9A.
Figure 9C:
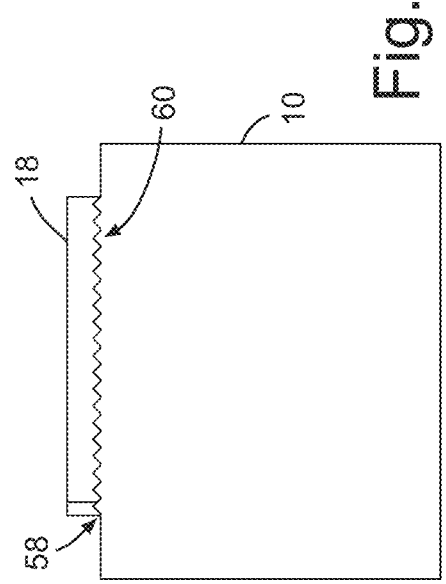
FIG. 9C is a side elevation view of the PCR cassette and the hot block of FIG. 9A.
Figure 9F:
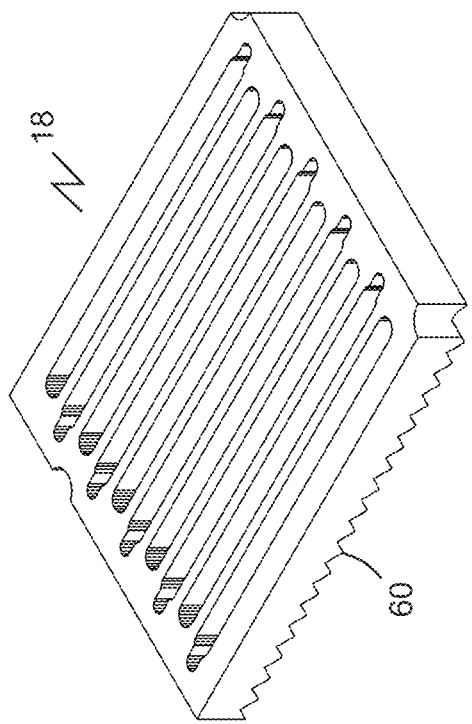
Figure 9E:
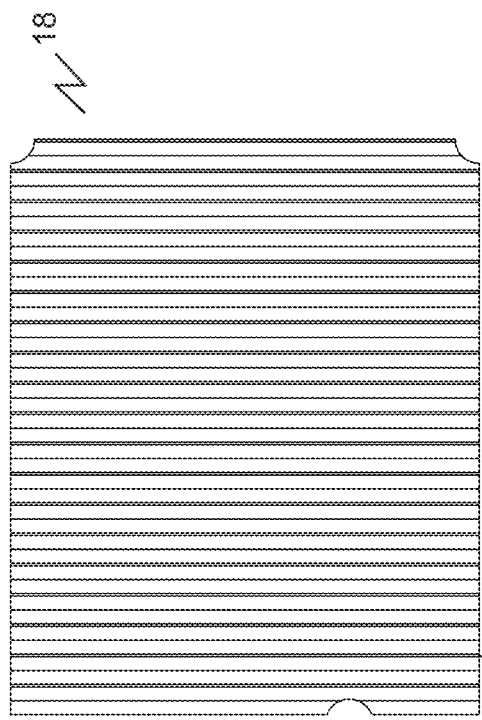
Figure 9G:
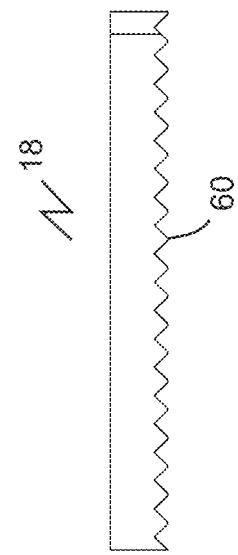

Referring to FIGS. 9A-9D, thermal performance may be impacted by adopting other contacting surface shape profiles, for example grooves, heat transfer fins, or rails, that enhance the surface contact area to volume ratio. One or both of the heat transfer surfaces 16 or a block contacting surface 19 of the PCR reaction cassette 18 may be shaped to increase surface area relative to a planar surface. Referring to FIGS. 9A-9C, the heat transfer surfaces 16 and a block contacting heat transfer surface 19 (collectively the corresponding heat transfer surfaces) of the PCR reaction cassette 18 may be structured with matching shapes, for example complementary nesting shapes. Block 10 may have a grooved mating surface 58. Referring to FIGS. 9A and 9C-9D, cassette 18 may have a corresponding grooved mating surface 60. Referring to FIG. 4 by contrast, block 10 may have a planar (flat and level in some cases) top loading surface 16 due to its comparative ease of fabrication, reduced thermal losses and quick adaptability to different cassette 18 profiles. One or both of the heat transfer surfaces 16 or the block contacting surface of the PCR reaction cassette 18 may have a planar shape. In some cases, PCR reaction cassette 18 has a plate shape that defines an external block contacting surface.

Overhanging hot surfaces above the cassette 18 may be added to create a more oven-like environment for the cassette 18, for example to improve temperature compliance. Primary heating and cooling of the cassette 18 may still be provided primarily by the broad contact area between the cassette 18 and hot block 10, but the presence of a broad face above the cassette 18 that was warmed to the target temperature of the underlying hot block 10 may help suppress radiative and convection losses from the cassette 18 and thus improve temperature slewing rates and reduce any residual temperature gradients across the PCR working volume. A simple variation on this is included in the tested prototype units in the form of a static cover window positioned over the hot block working area. This window is spaced sufficiently to allow the cassette 18 to slide sideways underneath, but is close enough such that a bolus of warm air builds up above the hot block surface and warms the glass, which from both effects helps thermally stabilize the cassette 18. This reasoning may be extended to providing a full clamshell clamp arrangement at one or more hot blocks 10 which would be activated when the cassette 18 moved into position. Coordination of the clamping and movement of the cassette 18 may be accomplished by a suitable means. However, the pre-bias and/or preheat techniques may still be applied if the clamp features were suitably temperature controlled and had thermal characteristics similar to those required of the hot blocks 10 already described.

Good thermal contact between the cassette 18 and the hot block 10 may be maintained by one or more of simple gravity forces (the weight of the cassette 18), added magnetic clamping forces acting between permanent or switched electromagnets incorporated in various faces of the hot blocks 10 and the cassette 18, mechanical clamping devices, use of vacuum chuck features to draw the cassette 18 down with atmospheric pressure, and other suitable means. Thermal contact may also be enhanced by adding a thin film of thermal couplant such as a drop of oil, to displace air from small gaps between the cassette 18 and hot block 10 surfaces. Further, in the above option of incorporating mechanical clamping features, these could be actively temperature controlled and used to recruit portions of the top and side surfaces of the cassette 18 as added thermal contacts.

Referring to FIGS. 7A-7B, a linear stage or linear array configuration or incarnation in which cassette 18 moves back and forth across the different hot blocks 10, for example in directions 90 is shown. Such a configuration may be suitable for low rate of test requirements. Hot blocks 10 may have other arrangements. In some cases, hot blocks 10 have circular and/or looping hot block configurations in which the cassette 18 moves only in one direction. Hot blocks 10 may have symmetrical linear arrangements where the cassette 18 moves between two distal hot or cold ends through a central zone with the complimentary temperature. Hot blocks 10 may be part of systems designed to move the hot blocks 10 with the cassette 18 remaining relatively motionless. Hot blocks 10 may have configurations where multiple cassettes 18 are "in-flight" at the same time so that testing can be pipelined to improve system throughput, for example with several cassette 18 staggered around a turntable arrangement of pie shaped hot blocks, so that although the PCR tests would complete one-at a time, they would follow closely one after the other.

One potential issue associated with a simple back and forth linear cassette 18 motion is shading. Shading may result from one edge of the cassette 18 experiencing a longer exposure to one temperature than the other edge experiences. This may occur at the end of travel in each direction on a linear hot block arrangement because the cassette 18 has to reverse direction to continue the cycling. In that case, the edge of a cassette 18 that is first to arrive on an end most hot block is also the last to leave. In practice, the transit time onto or off of a particular hot block may be short compared to the thermal equalization time measured at the PCR region and then subsequently the additional dwell time typically included in the process to accommodate the molecular chemistry for that step to run its course. Also, since the cassette 18 may be relatively conductive, the transient gradients produced in the direction of motion may be suppressed somewhat, especially so if there is a small thermal conductivity reduction right at the mating interface, which in practice may exist to some degree as the cassette 18 has to slide on a very thin air gap or couplant film layer.

Another physical arrangement that may mitigate the shading issue is using a rotary hot block design. In this instance, the hot blocks 10 are fabricated with a pie wedge shape and arranged around a circular path. A central axle or outer drive ring may be used to shuttle the cassette 18 around in either a step wise stop-and-go fashion, a ballistic (constant magnitude of acceleration) speed-up and slow-down mode or even a steady speed circle motion (depending on the rotation speeds, sizes of the blocks, drive mechanisms and other similar design factors commonly considered) so that the leading and trailing edges of the cassette 18 have essentially the same residence time on a particular hot block. Note that some second order shading effects may still occur, especially if the samples volumes are not shaped and oriented to take advantage of the radial geometry.

There may also be other opportunities to reduce shading effects in the linear arrangement, one of which is taken advantage of in the present prototypes. The hot blocks 10 are larger than the mating face of the cassette 18. This was done partially to improve the uniformity of the hot block surface temperature (by moving the non-ideal edge effects further out from the central resting spot of the cassette 18) but also to give the cassette 18 some room to pick up speed or slow down while still substantially on the hot block surface. This has the effect of making the transition from one block to the other appear much faster since the cassette 18 is at peak velocity as is crosses over the space between hot blocks. In some cases the series of blocks are arranged in a loop, an arc, or a linear array, and an actuator directs the movement of the PCR reaction vessel along the shape of path.

Other motion systems may also incorporate a break before mating style of coupling in which, as the cassette 18 is moved from its central mated position on a hot block, it is gently lifted to form a gap as it is shifted over before sitting down again on the next block.

Coordinating the cassette 18 movement and temperature settings of the rotary configured hot blocks 10 would follow essentially the same logic as discussed for the linear arrangement as would the discussions around the design, sizing and configuration of the individual pie sections. Ultimately, the particular design direction regarding linear versus rotary may depend on other application objectives and might reasonably fall either way.

In this regard, no limitation on this disclosure is implied by the discussions emphasizing one style of motion over the other as either may be used to good effect.

Figure 6:
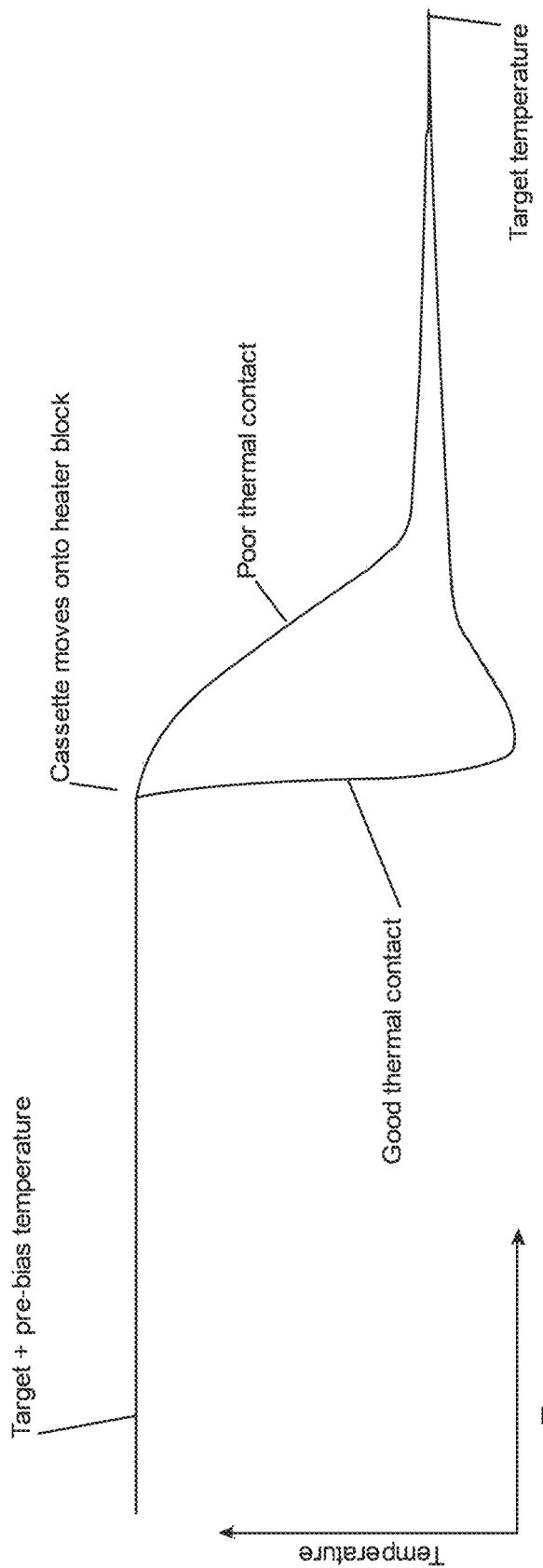
FIG. 6 is a graph illustrating heater block temperature when a PCR cassette having a lower temperature moves onto the block.

Various process diagnostic features may be available as a result of the underlying technique. For example, closely monitoring the hot block temperature behaviour as a cassette 18 moves onto it (not restricted to or limiting on the disclosure, but typically, for several seconds before and for 10 to 15 seconds following), shows a time evolution of the temperature disturbance induced in the hot block 10 provides a strong indicator of the thermal bond quality between the cassette 18 and the hot block 10. This is shown schematically in the expanded view of one of the idealized temperature transitions from FIG. 5, shown expanded in FIG. 6. A solid bond provided by well-matched contact surfaces without any air gaps or contamination may give a relatively rapid temperature change seen at the temperature sensor in block 10 that settles relatively quickly to the equilibrium temperature of the two pieces. A poorer bond may demonstrate a slower temperature change, as the thermal equalization takes more time to settle. The overall area under the impulse and the final convergence value of the temperature may also indicate cassette 18 fill issues. Monitoring the thermal mass (by way of assessing the thermal responsivity of the hot blocks to the cassette 18 arrival) may prove to be a useful diagnostic for several intended applications where any significant loss of PCR reagents or process materials through evaporation or spillage may degrade the PCR results.

Other embellishments may optionally be incorporated into the system thermal control process. In many cases the power output of the individual hot block heaters, for example heaters 38 may be well known, as may be the case for instance when using voltage regulated power supplies operating good quality resistors in a pulse width modulated or bang-bang modulation scheme. In such situations, it may be reasonable to monitor the average duty factor required to hold the hot blocks 10 at their nominal set points and thus have some knowledge of the conductive and convective losses for the blocks 10 at their working temperatures under the current ambient conditions, and then to declare these duty factors as the reference baseline values for each hot block 10.

Given that the physical geometry and materials of construction will be known to a high degree of accuracy, it may then be possible to predict the proper amount of heat energy that must be added or subtracted to accomplish a given step change in block 10 temperature. The change of the block 10 temperature from target temperature when the cassette is on the block to the necessary pre-bias temperature before a cassette 18 arrives is potentially such a step change. Once the net energy change is known, the necessary decrease or increase in the heating or cooling power can be determined to supply or remove a bolus of heat that will let the block 10 temperature settle before the cassette 18 returns.

Although a configuration of this disclosure may have both the hot block 10 and the cassette 18 features, the underlying method of operation of each independently could be used in other implementations to retain some of the benefit provided by each independently. That is, in a system where the hot blocks 10 is replaced by a Peltier style heat-cool system, the high thermal conductivity cassette 18 of this disclosure could improve temperature response and gradient performance due to the intimate and highly conductive thermal bond it provides between the base and PCR region. Alternately, other common PCR vessels such as plastic microtiter plates, or glass or plastic micro-well arrays, may be processed using just the hot block 10 concept with appropriate adjustments for equalization timing and pre-biasing for the associated thermal mass, and recognizing that ramp rates and response times might suffer. Either of these concepts may be used to gain advantages separately.

Figure 10:
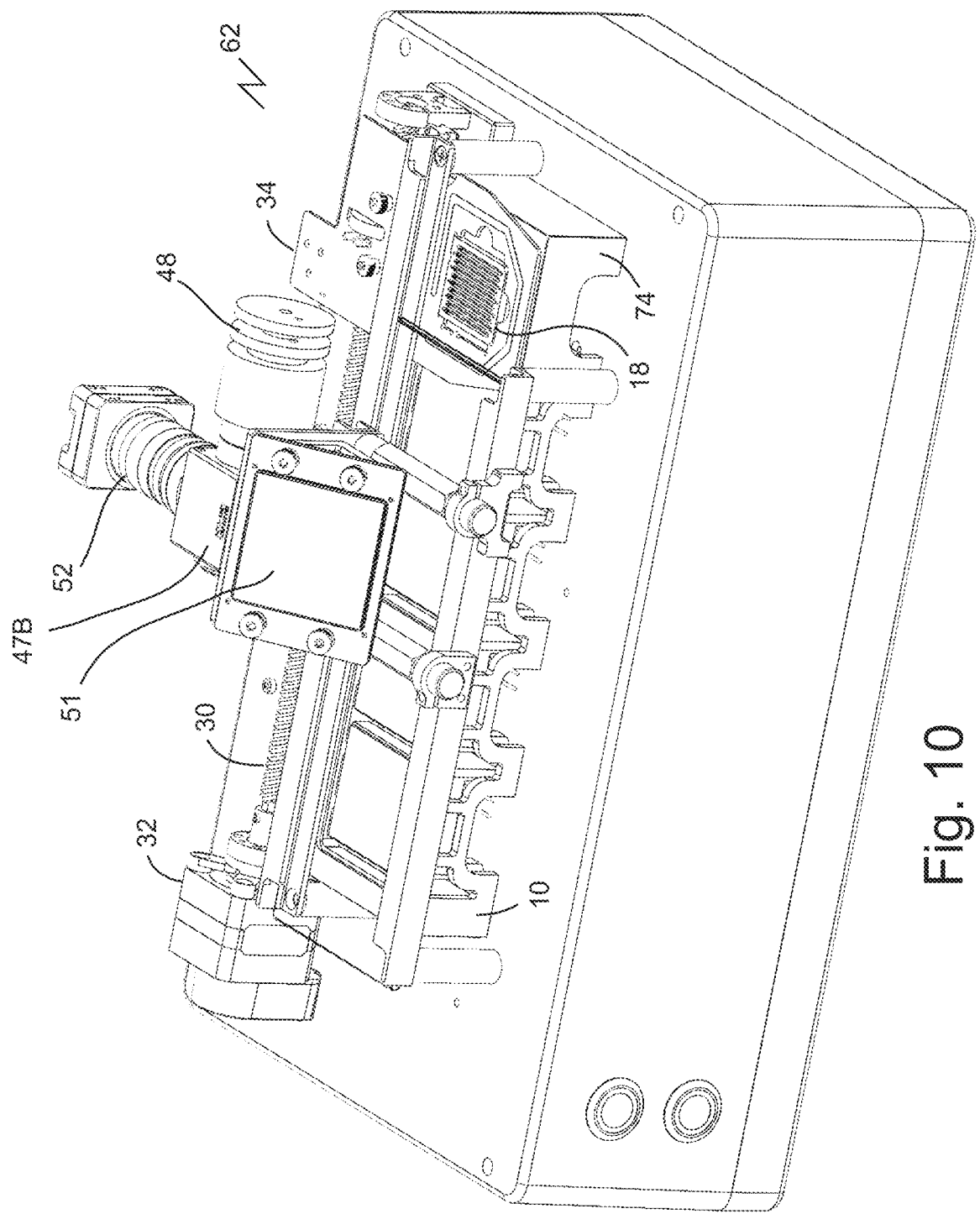
FIG. 10 is a perspective view of an operational prototype PCR system physical arrangement.
Figure 11:
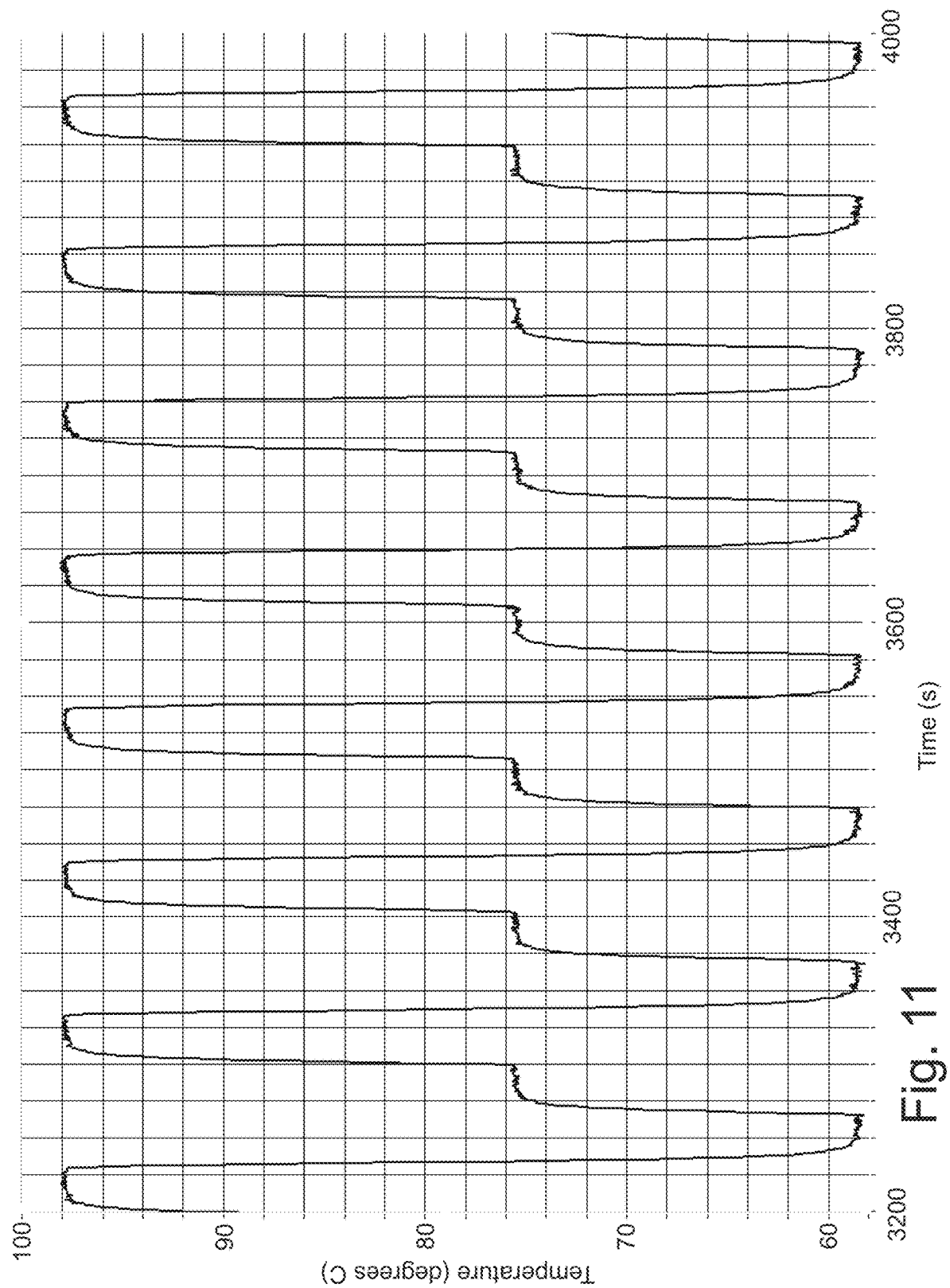
FIG. 11 is a graph illustrating measured temperature over several cycles at centre of PCR sample volume.
Figure 12:
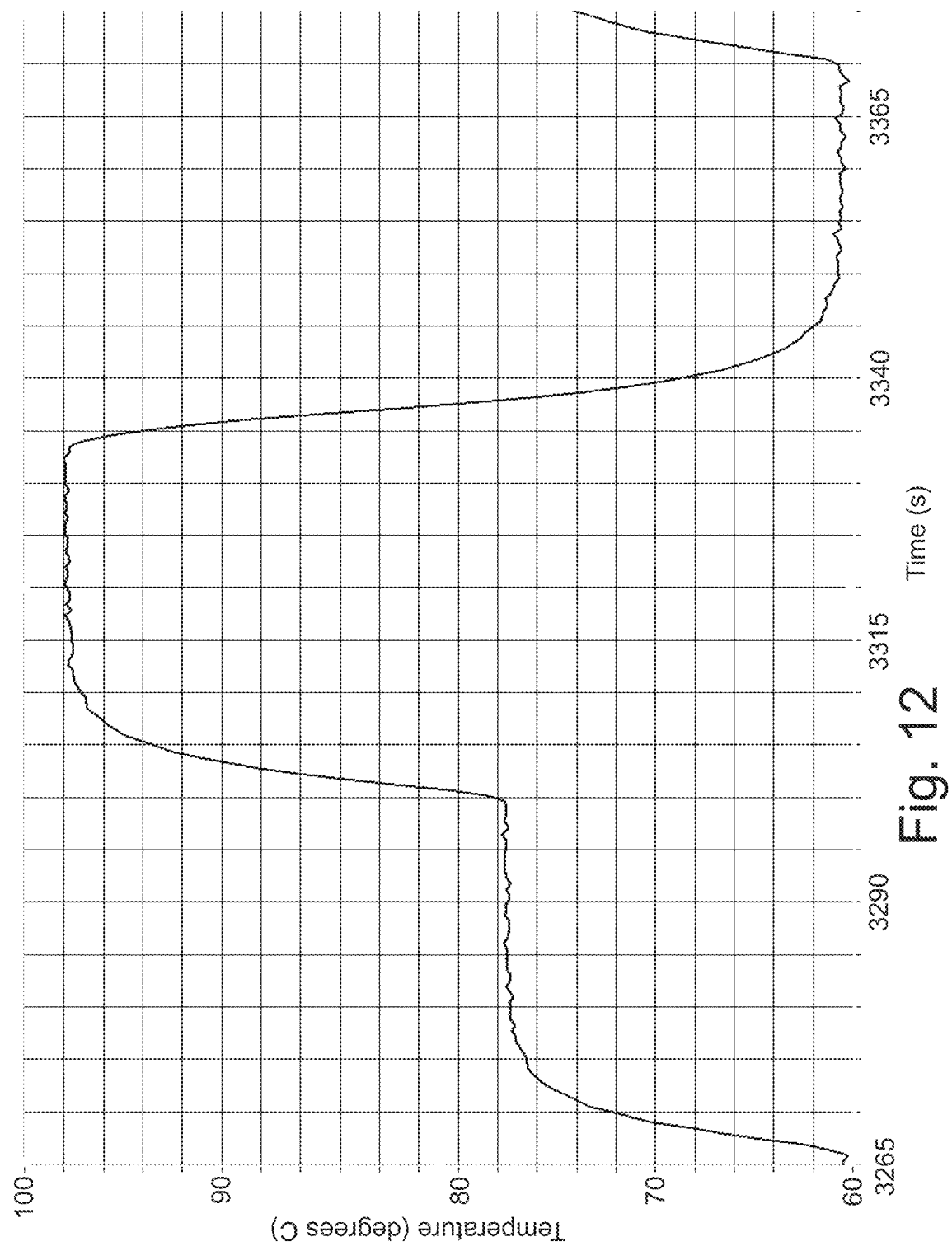
FIG. 12 is a graph illustrating an expanded view of one thermal heating stage in a single PCR cycle.
Figure 13:
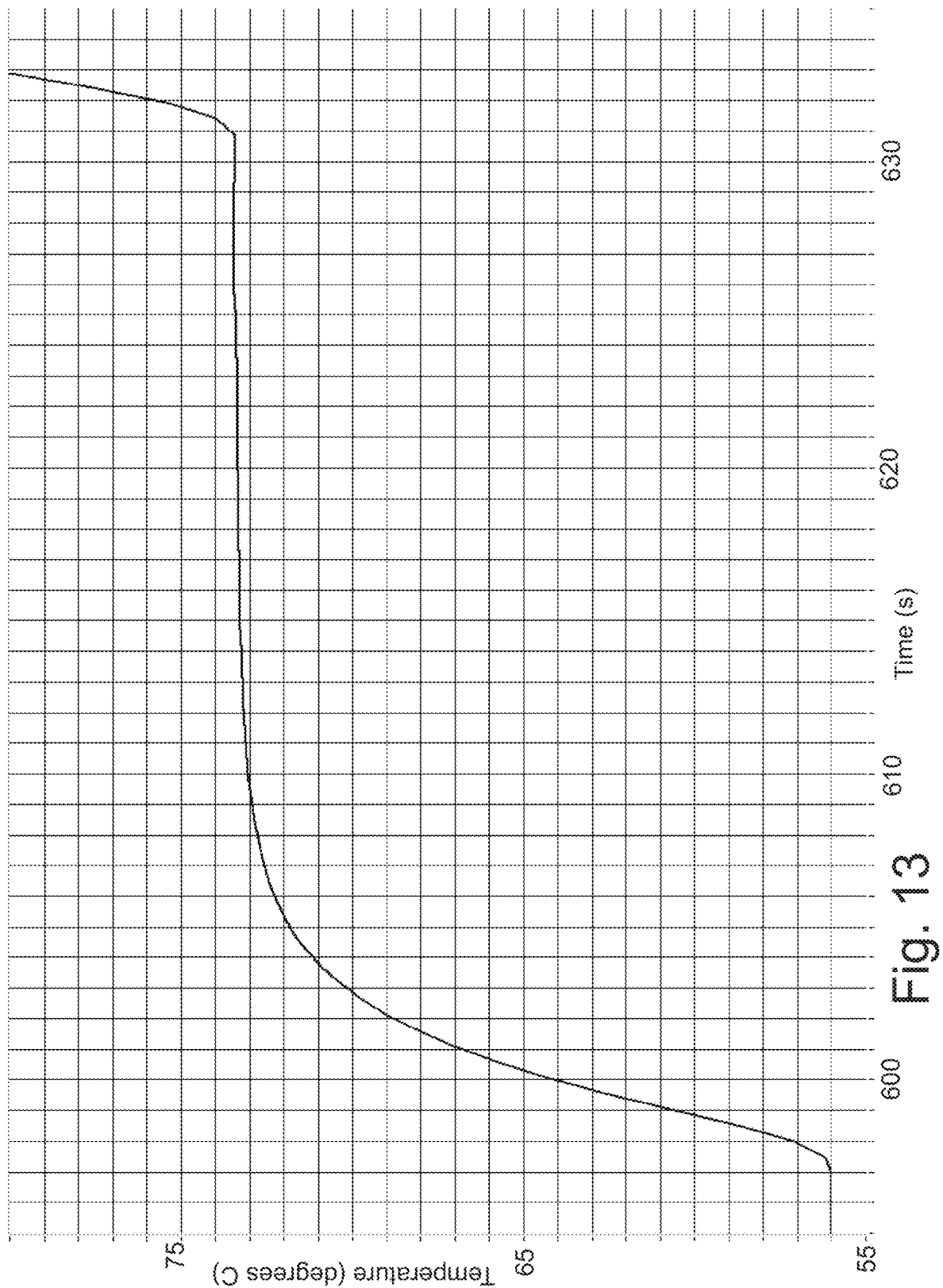
FIG. 13 is a graph illustrating an expanded view of the extension step of a PCR thermal cycle.

Several working prototypes have been made to evaluate and measure the capabilities of this disclosure. Referring to FIG. 10, a comprehensive physical unit 62 is shown, with such reflecting a reduction to practice of the system shown schematically in FIG. 8. The unit 62 may utilize one hot block 10 for each of the Annealing and Extension steps and a pair of blocks 10 for the Denaturation step. The two lower temperature hot blocks 10 may be operated using the pre-bias technique, while the paired set may use the pre-bias concept on the first of the two blocks 10 and the second block 10 of the two may be left at the target temperature. To verify the expected operation and fine tune the cassette 18 motion and temperature settings, the temperature within a representative PCR sample processing region of a cassette 18 may be collected over a series of trial runs. These temperatures may be measured using a small thermistor positioned in a representative central region of the PCR sample volume, and the thermistor may be spaced away from the walls 24, for example metal walls, of the cassette 18 by materials with thermal properties consistent with well hydrated sample. Typical data is shown in FIGS. 11, 12 and 13 for various time and temperature scales. Overall cycle time was roughly 105 seconds (s), however 75 s of this the cassette 18 is very close to the target temperature (dwell time), leaving the cumulative time spent completing the three main temperature transitions at about 30 s. This corresponds to 80° C. of net difference for a useful slew rate in the actual PCR sample processing region of 2.7° C. per second. These runs were completed using pre-bias settings selected for zero overshoot as is clear from FIG. 12 (giving an appearance similar to traditional overdamping). However, if some minor overshoot is allowed (leaning toward a critical damping situation), settling times may be improved.

Referring to FIGS. 8 and 10, the thermal cycler may comprise various systems to analyze the PCR process. For example, an epifluorescence assembly is shown comprising a camera 52, a dichroic mirror 47, an LED 48, LED drive circuitry 50, a photodiode 46, filters, and other optics such as lenses 49; and a viewing mirror 51. A computer 56 or other controller may be provided for overall control of the system and data collection. The purpose of an epifluorescence assembly is to allow a melt curve to be made on the same device as the PCR process, once the PCR cycling has completed, or at intermediate stages in the process to track progress. A light source or other illumination assembly may be provided, for example comprising LED 48 to expose the cassette 18 to fluorescence inducing light, and various optics. A camera 52 may be provided to view the cassette contents. A dichroic mirror 47 (with or without a dichroic mirror mount 47B) or other suitable optics may be provided to route illumination and fluorescence image as shown in FIG. 8. A viewing mirror 51 may be provided to permit a user to inspect and rotate imaging and illumination axis. The epifluorescence system may use heat from one or more of the hot blocks 10 to carry out the melt curve analysis, and the controller may coordinate the heating of the respective block 10 with the fluorescence and imaging process. After the last cooling step in the PCR, the cassette may be moved under the camera view, the illumination is activated and a series of images taken as the cassette is warmed back up until all the tagged DNA denatures. Depending on the temperature that the tagged DNA melts, as seen by a sudden loss of the fluorescence signal at the camera, the user may be able to identify if a particular type of DNA is present, thus achieving a diagnostic use of the system.

Note that the temperatures and number of thermal cycles shown on the charts are intended only to demonstrate a notional PCR thermal cycling run. The process sequence definition parameters may be readily adjusted to suit the needs of a particular molecular chemistry, such as (commonly) configuring dwell times, the number of cycles and target temperatures. However, in more complex implementations, various additional features may be optionally added to the sequence, including inserting intermediate melt curve measurements into the PCR thermal cycle sequence, varying the relative timing of steps, or modifying the target temperatures during the course of the thermal cycling sequence.

Power consumption during initial warm up peaked at roughly 105 W at start-up, which persisted for about 8 minutes and then began to taper off to around 50 W by 30 minutes in warm up. Average power consumption during thermal cycling will be only slightly higher than 50 W. Power during the final melt curve measurements increased slightly, but this function only runs for 5-10 minutes per test sequence. From a practical standpoint, these power consumption results are on the order of a factor of 5 to 10 lower than most specification sheet ratings on commercial thermal cycling products available on the market. This power level is also consistent with mobile or portable battery operated applications. These figures demonstrate the inherent comparatively low power operation capability of such an approach, making it far more amiable to battery portable equipment applications. In some cases the thermal cycler is provided as a portable unit with an internal battery as a power source.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A thermal cycling method for carrying out a polymerase chain reaction (PCR) process to amplify deoxyribonucleic acid (DNA), the method comprising:

pre-heating a series of blocks to respective temperatures that correspond to different respective heating stages in a PCR process, in which each block of the series of blocks defines a respective heat transfer surface, in which the series of blocks define a sequence of positions along a path, with each position defined by a respective heat transfer surface of a respective block; and moving a PCR reaction vessel, which contains deoxyribonucleic acid (DNA) and PCR reagents, along the path into and out of each respective position in the sequence of positions according to a schedule, in which, at each respective position the PCR reaction vessel is in thermal contact with the respective heat transfer surface to equilibrate a temperature of the PCR reaction vessel to a target temperature that corresponds to a respective heating stage in the PCR process;

in which pre-heating comprises pre-biasing the temperature of the respective block, prior to the PCR reaction vessel moving into thermal contact with the respective heat transfer surface of the respective block, the respective block corresponding to a respective heating stage and respective target temperature of the PCR reaction vessel in the PCR process, in which the temperature of the respective block is pre-biased to a pre-bias temperature that is either:

a) below the respective target temperature if the PCR reaction vessel has a temperature that is higher than the respective target temperature as the PCR reaction vessel moves into the respective position, or b) above the respective target temperature if the PCR reaction vessel has a temperature that is lower than the respective target temperature as the PCR reaction vessel moves into the respective position, in which, upon making thermal contact with the PCR reaction vessel, the respective temperature, of the respective block whose temperature was previously pre-biased above or below the respective target temperature of the respective block, is subsequently changed from the pre-bias temperature to be at, and thereafter maintained at, the respective target temperature, which is different than the pre-bias temperature;

in which a thermal mass of each block is such that each block has a mass ratio as low as 15:1 and as high as 100:1 relative to a thermal mass of the PCR reaction vessel, in which the pre-bias temperatures are calculated based on the temperature of the PCR reaction vessel as it is incoming, the respective target temperature and the relative thermal masses of the PCR reaction vessel and the respective block.

2. The thermal cycling method of claim 1 in which, in each respective position, a base heat transfer surface of the PCR reaction vessel is in thermal contact with the respective heat transfer surface, which faces up.

3. The thermal cycling method of claim 1 in which:
the heat transfer surfaces define a common plane in which the path is defined; and
each block in the series of blocks is thermally isolated from adjacent blocks.

4. The thermal cycling method of claim 1 in which moving is carried out by an actuator, which is connected to a controller that implements the schedule.

5. The thermal cycling method of claim 1 in which moving comprises moving the PCR reaction vessel between:
a first position where the PCR reaction vessel is in thermal contact with a first block that equilibrates the PCR reaction vessel at a first target temperature sufficient to denature the DNA;
a second position where the PCR reaction vessel is in thermal contact with a second block that equilibrates the PCR reaction vessel at a second target temperature sufficient to anneal primers to denatured DNA; and
a third position where the PCR reaction vessel is in thermal contact with a third block that equilibrates the PCR reaction vessel at a third target temperature sufficient to cause polymerized extension of the DNA.

6. The thermal cycling method of claim 1 in which the magnitude of pre-bias is optimized to prevent a reaction zone of the PCR reaction vessel from:
overshooting the respective target temperature in the case where the respective block is pre-biased above the respective target temperature; and
undershooting the respective target temperature in the case where the respective block is pre-biased below the respective target temperature.

7. The thermal cycling method of claim 1 in which the direction and magnitude of the pre-bias is selected to achieve an equalization temperature in the PCR reaction region that is equal to the respective target temperature after thermal contact and settling of the PCR reaction vessel with the respective block.

8. The thermal cycling method of claim 1 in which a transitional block is positioned adjacent and upstream of a respective position along the path, and further comprising, before the PCR reaction vessel reaches the respective position, pre-heating or pre-cooling the PCR reaction vessel in the direction of a respective target temperature of the respective position by heat transfer across a heat transfer surface of the transitional block as the PCR reaction vessel comes into thermal contact with the transitional block.

9. The thermal cycling method of claim 1 in which the thermal mass of each block is between 15:1 and 35:1 relative to a thermal mass of the PCR reaction vessel.

10. The thermal cycling method of claim 1 in which each block is made of relatively high thermal conductivity and high thermal capacity material.

11. The thermal cycling method of claim 1 in which the PCR reaction vessel is made of relatively high thermal conductivity material.

12. The thermal cycling method of claim 1 in which one or both of corresponding heat transfer surfaces of the block and the PCR reaction vessel are shaped with complementary features to increase the contacting face surface area relative to a planar surface.

13. The thermal cycling method of claim 1 in which corresponding heat transfer surfaces of the block and the PCR reaction vessel are planar in shape and the PCR reaction vessel is formed as a thin plate with respect to the transfer surface size.

14. The thermal cycling method of claim 1 in which the series of blocks are arranged in either a loop, an arc, or a linear array, and an actuator directs the movement of the PCR reaction vessel along the shape of path.

* * * * *